(12) United States Patent
Cha et al.

(10) Patent No.: US 12,226,535 B2
(45) Date of Patent: Feb. 18, 2025

(54) MICRONEEDLE ADHESIVE PATCH BASED ON HYDROGEL FORMULATION

(71) Applicant: POSTECH ACADEMY-INDUSTRY FOUNDATION, Gyeongsangbuk-do (KR)

(72) Inventors: Hyung Joon Cha, Gyeongsangbuk-do (KR); Eun Young Jeon, Gyeongsangbuk-do (KR); Jung Ho Lee, Gyeonggi-do (KR); Geun Bae Lim, Gyeongsangbuk-do (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 996 days.

(21) Appl. No.: 17/056,340

(22) PCT Filed: May 17, 2019

(86) PCT No.: PCT/KR2019/005952
§ 371 (c)(1),
(2) Date: Nov. 17, 2020

(87) PCT Pub. No.: WO2019/221559
PCT Pub. Date: Nov. 21, 2019

(65) Prior Publication Data
US 2021/0275359 A1 Sep. 9, 2021

(30) Foreign Application Priority Data
May 18, 2018 (KR) .......................... 10-2018-0057040

(51) Int. Cl.
| | |
|---|---|
| *A61L 15/32* | (2006.01) |
| *A61F 13/00* | (2024.01) |
| *A61F 13/02* | (2024.01) |
| *A61L 15/28* | (2006.01) |
| *A61L 15/58* | (2006.01) |
| *A61L 15/60* | (2006.01) |
| *A61M 37/00* | (2006.01) |

(52) U.S. Cl.
CPC ........ *A61L 15/32* (2013.01); *A61F 13/00063* (2013.01); *A61F 13/023* (2013.01); *A61L 15/28* (2013.01); *A61L 15/58* (2013.01); *A61L 15/60* (2013.01); *A61M 37/0015* (2013.01); *A61F 2013/00451* (2013.01)

(58) Field of Classification Search
CPC .......... A61L 15/32; A61L 15/28; A61L 15/58; A61L 15/60; A61L 15/42; A61L 15/585; A61L 15/64; A61L 24/0031; A61L 24/0042; A61F 13/00063; A61F 13/023; A61F 2013/00451; A61F 2013/0296; A61F 13/0246; A61F 2013/00676; A61F 2013/00906; A61M 37/0015; A61M 2037/0023; A61K 9/0021
See application file for complete search history.

(56) References Cited

U.S. PATENT DOCUMENTS

| | | | | |
|---|---|---|---|---|
| 2010/0114348 A1* | 5/2010 | Boyden | .................. | G16H 50/50 700/109 |
| 2015/0252148 A1* | 9/2015 | Lee | .......................... | A61L 27/56 435/395 |
| 2017/0190746 A1* | 7/2017 | Cha | ...................... | A61L 24/0015 |
| 2018/0021437 A1* | 1/2018 | Kim | ....................... | A61K 47/36 514/777 |

FOREIGN PATENT DOCUMENTS

| | | | | |
|---|---|---|---|---|
| CN | 108785753 | * | 11/2018 | |
| JP | 2017-176238 | * | 10/2017 | |
| KR | 10-2014-0027031 | * | 3/2014 | |
| KR | 10-2018-000477 | * | 1/2018 | |
| WO | WO-2011115420 A2 | * | 9/2011 | ........... A61L 27/227 |
| WO | WO-2016129967 A1 | * | 8/2016 | ............. A61K 47/36 |
| WO | WO-2017101024 A1 | * | 6/2017 | |

OTHER PUBLICATIONS

Chen et al., Adv. Drug Delivery Reviews 65 (2013) 1357-1369 (Year: 2013).*
Wikipedia Glycerol, downloaded Feb. 8, 2024 from the internet, six pages provided (Year: 2024).*
Wikipedia entry for Microneedle drug delivery, downloaded Feb. 7, 2024 from the internet (Year: 2024).*
English Machine Translation of JP2017176238 (Year: 2017).*
English Machine Translation of WO2017/101024 (Year: 2017).*
English machine translation of KR 10-2018-000477 A, Jan. 3, 2018 publication date (Year: 2018).*
English machine translation of KR 10-2014-0027031 A, Mar. 6, 2014 publication date (Year: 2014).*

* cited by examiner

*Primary Examiner* — Melissa L Fisher
*Assistant Examiner* — Joseph Fischer
(74) *Attorney, Agent, or Firm* — LEX IP MEISTER, PLLC

(57) ABSTRACT

Disclosed are a microneedle patch including a first hydrogel layer containing a mussel adhesive protein and hyaluronic acid, and a second hydrogel layer containing silk fibroin, and a preparation method thereof. The microneedle patch according to the present disclosure has excellent tissue adhesion, biocompatibility, and biodegradability, and is used for transdermal drug delivery to promote wound regeneration.

10 Claims, 9 Drawing Sheets
Specification includes a Sequence Listing.

[Figure 1]
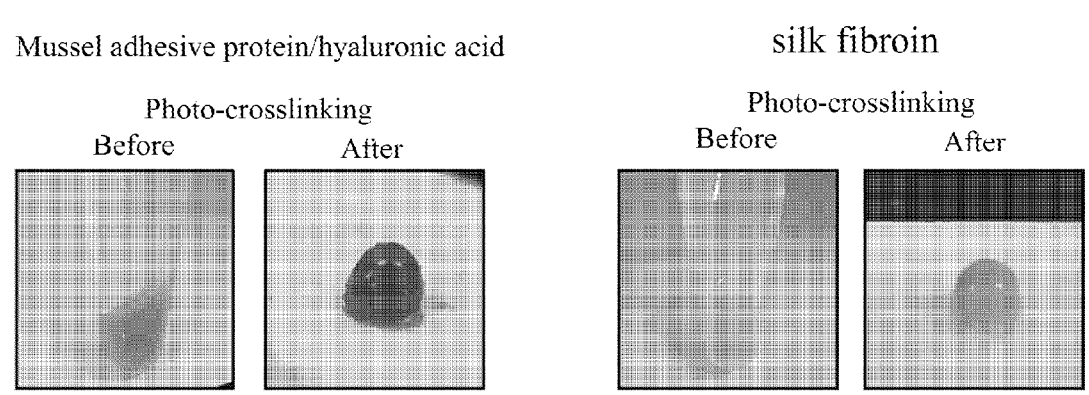
[Figure 2]
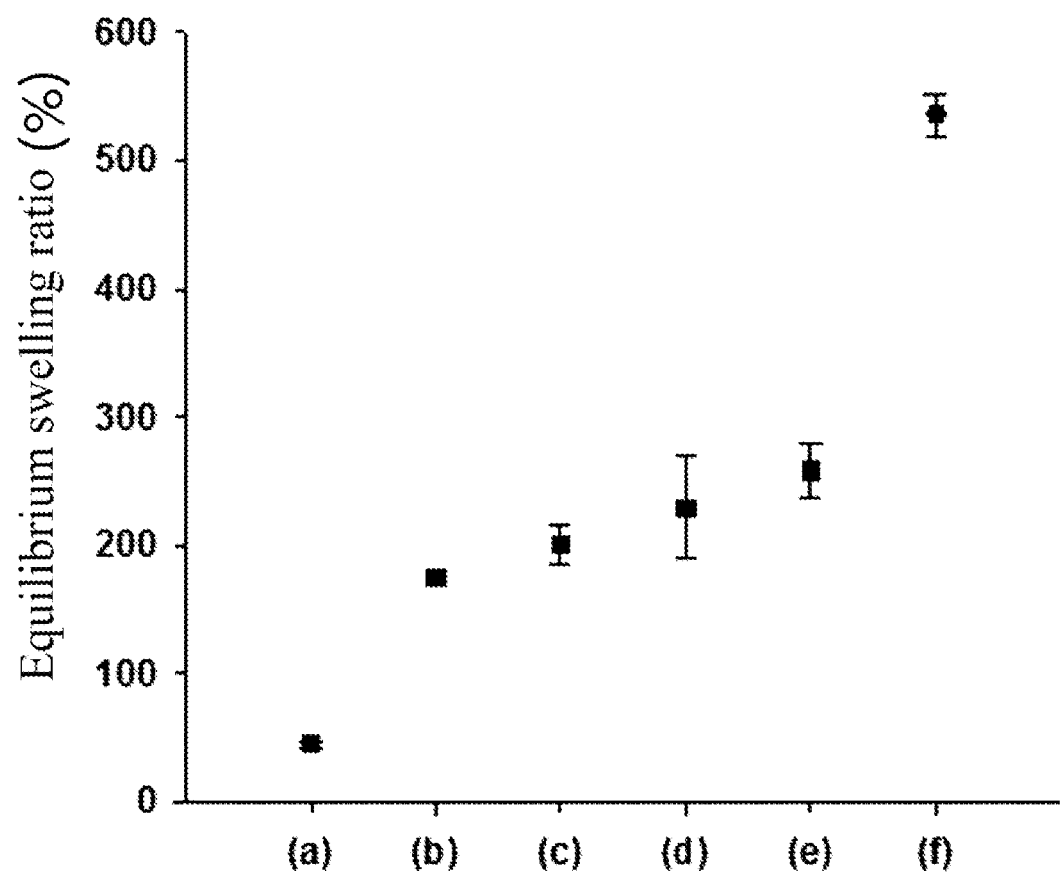

[Figure 3]
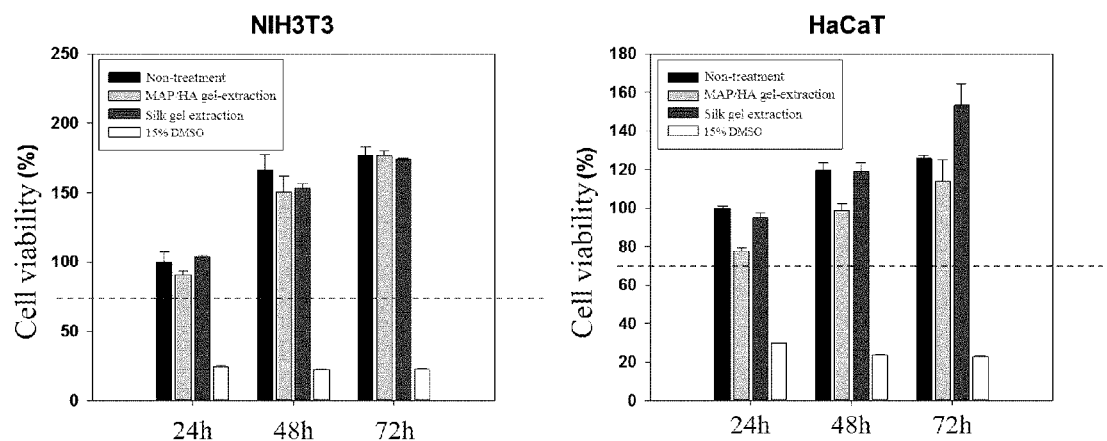
[Figure 4]
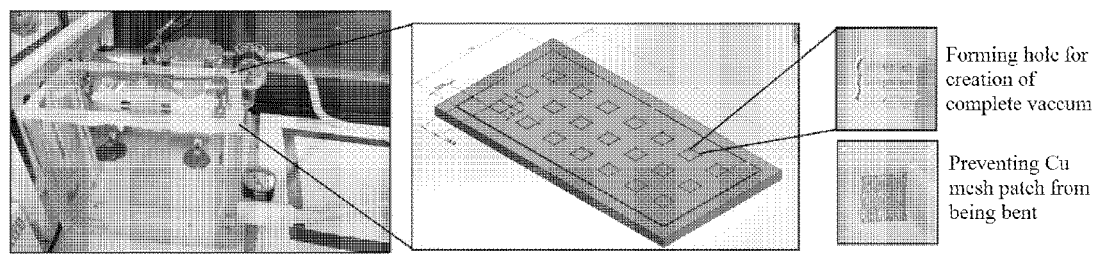

[Figure 5]
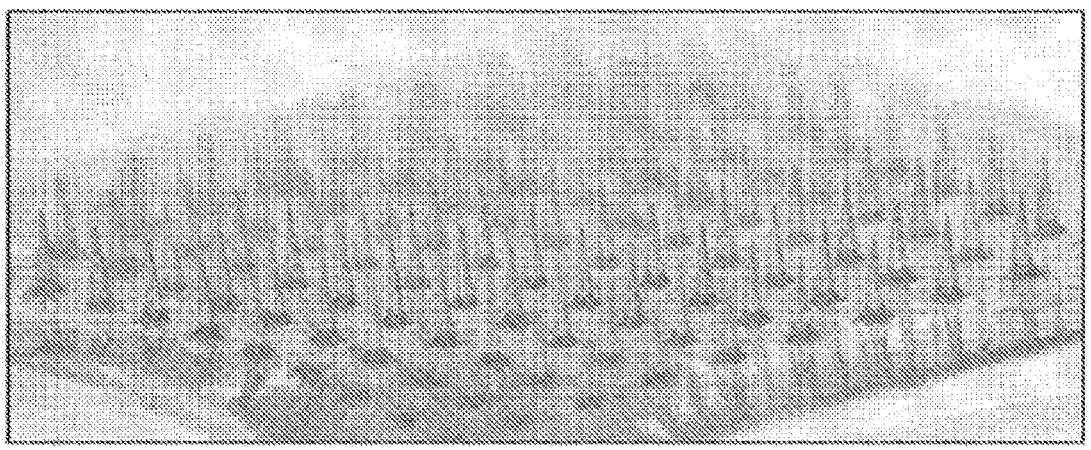
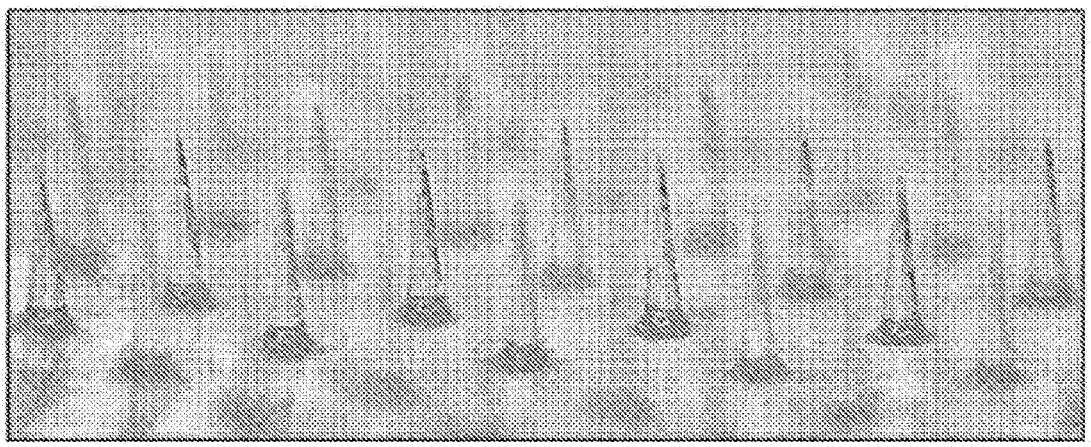

[Figure 6]
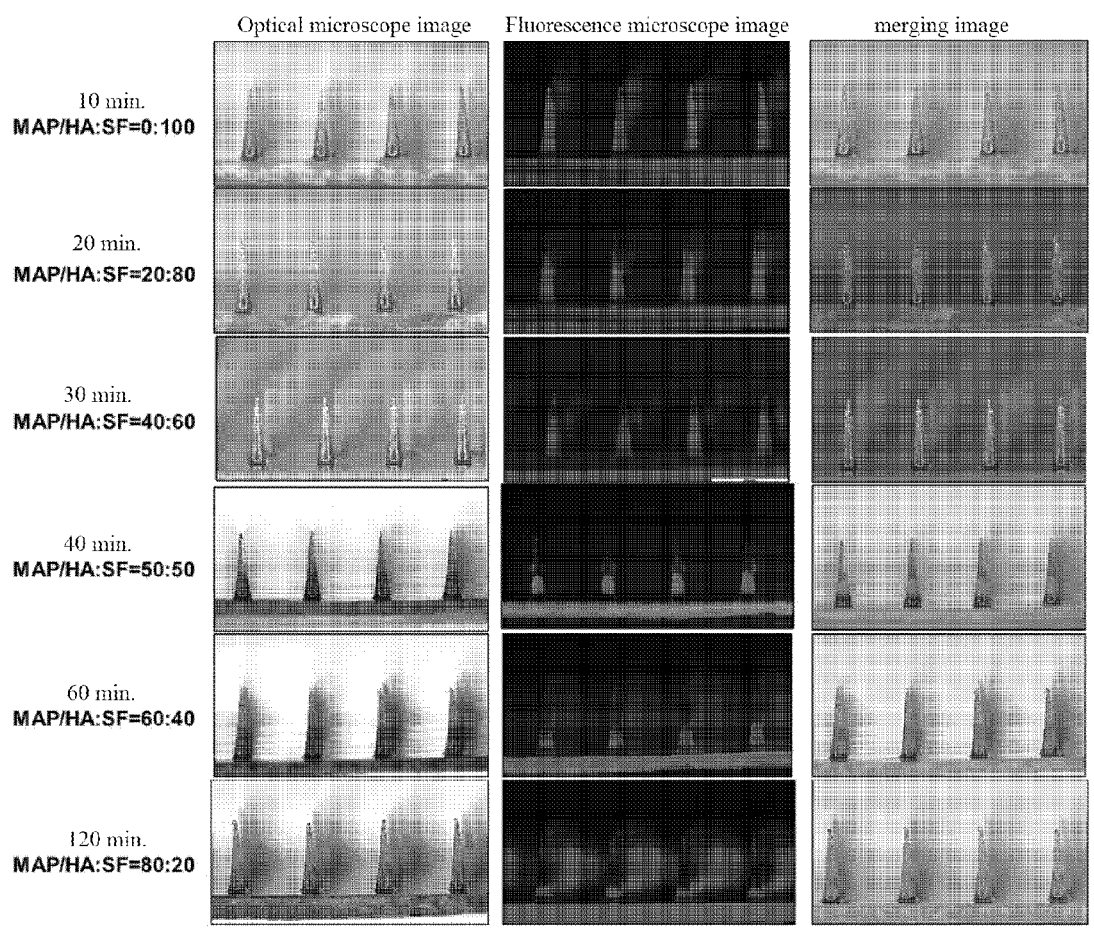

[Figure 7]
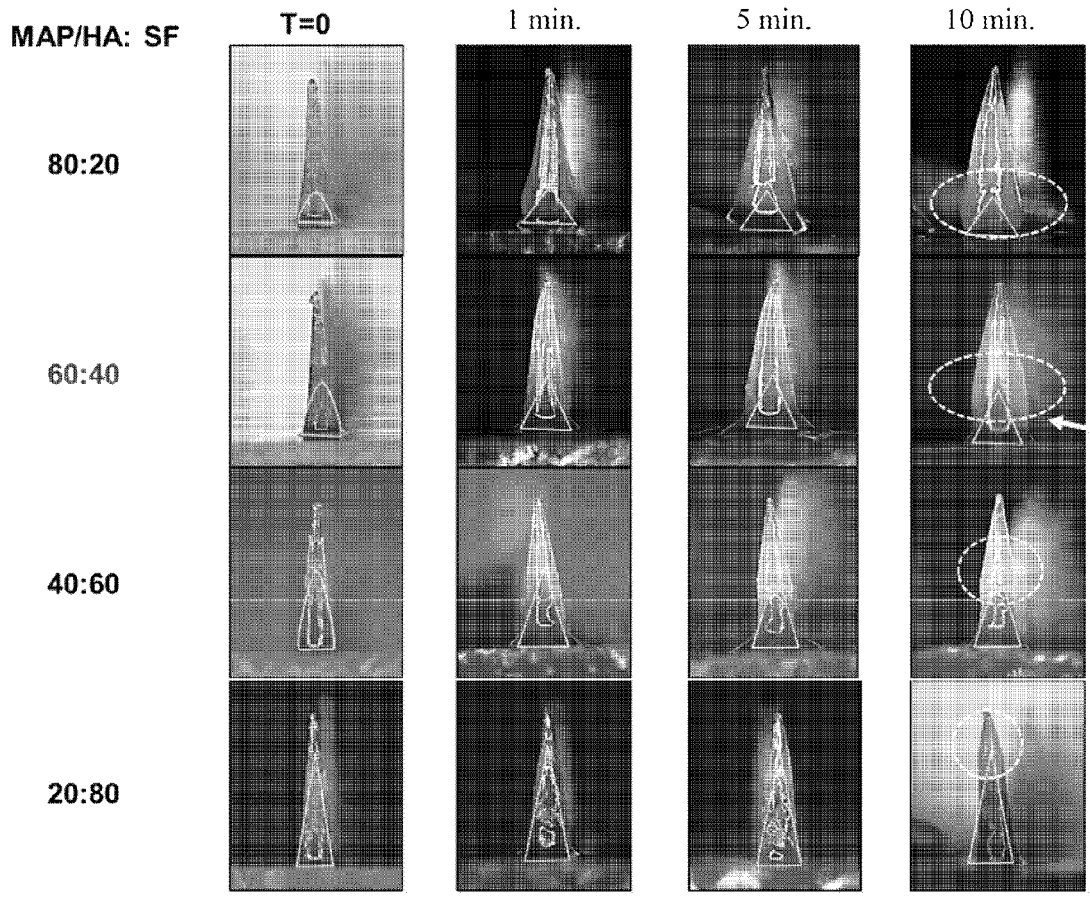
[Figure 8]
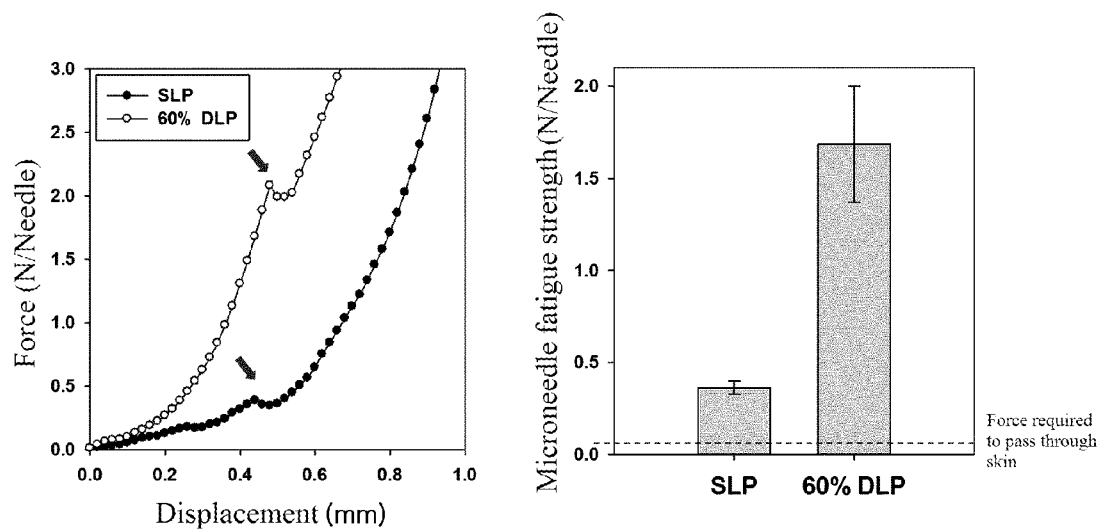

[Figure 9]
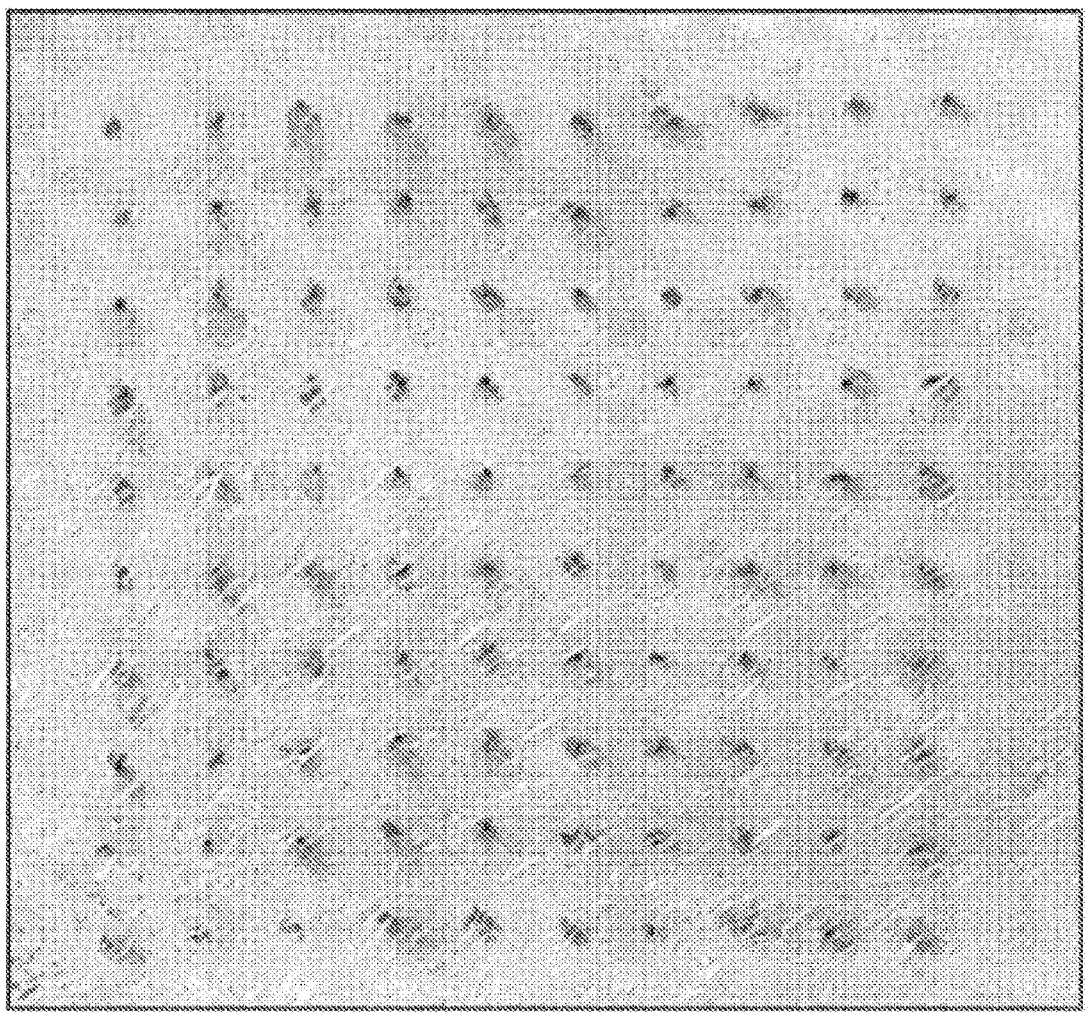

[Figure 10]
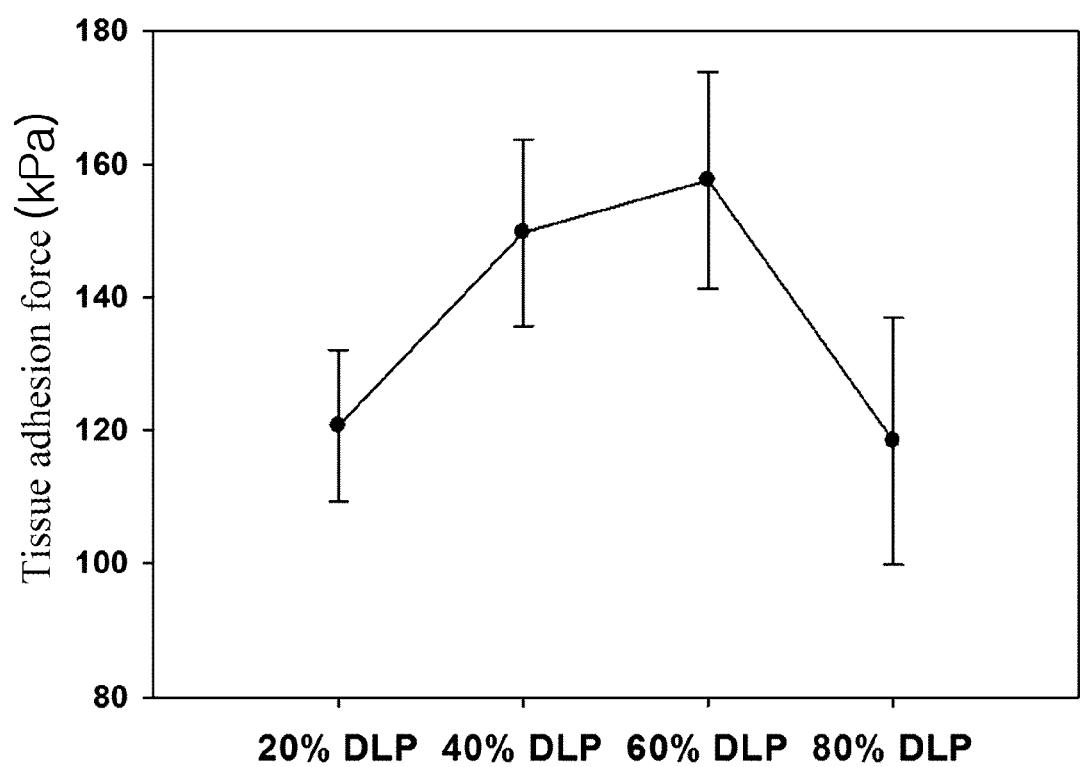

[Figure 11]
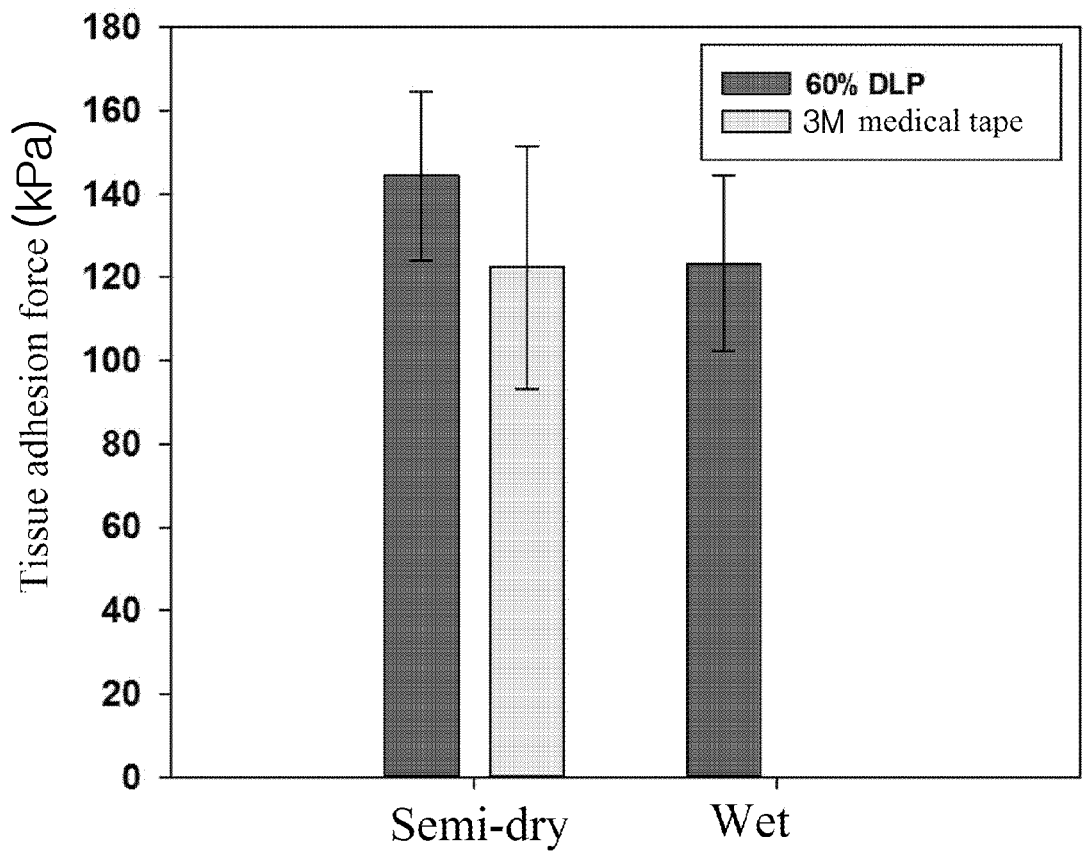
[Figure 12]
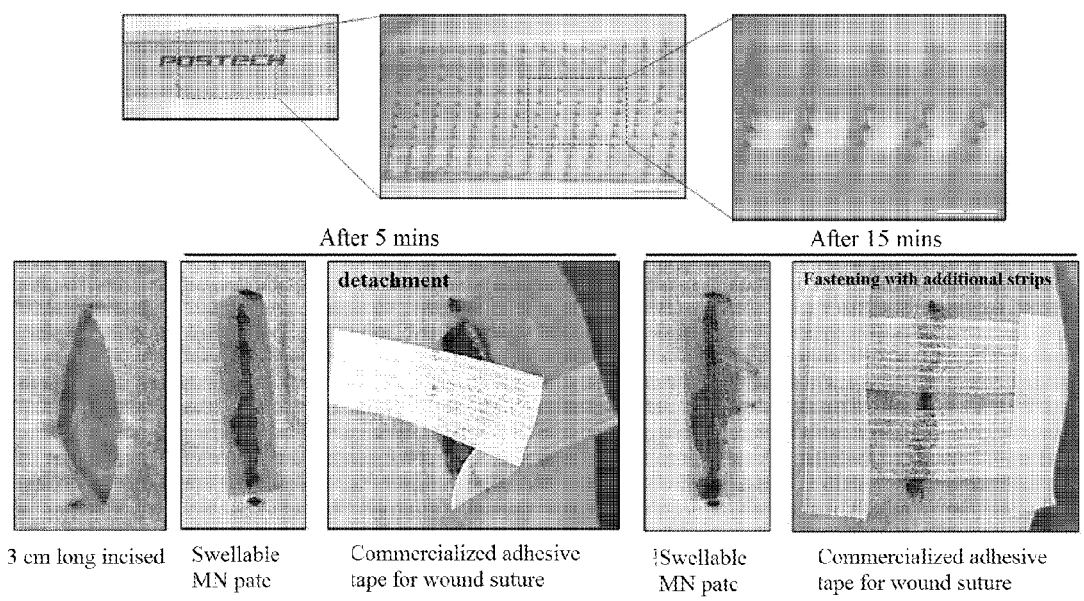

[Figure 13]
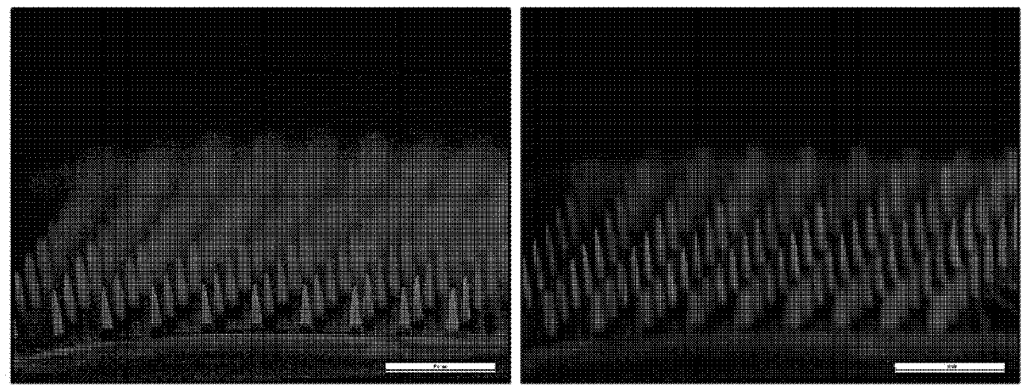
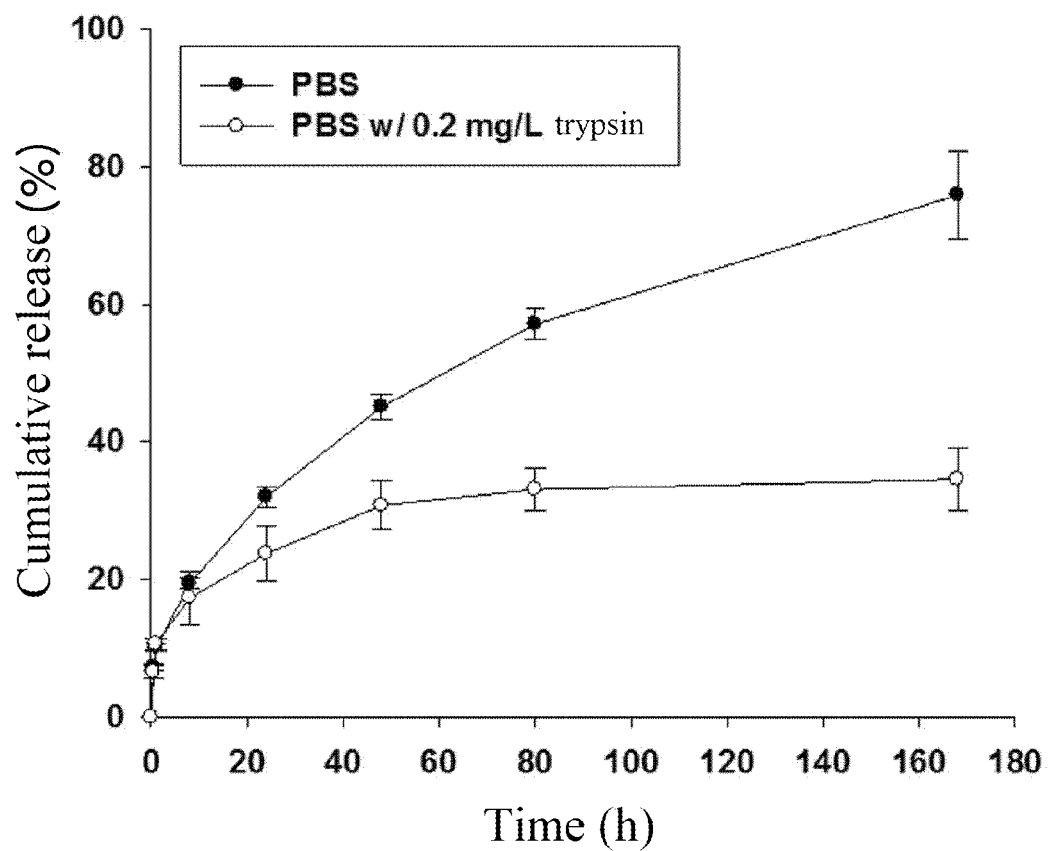

MICRONEEDLE ADHESIVE PATCH BASED ON HYDROGEL FORMULATION

CROSS-REFERENCE TO RELATED APPLICATIONS

This is a U.S. National Phase of International Application PCT/KR2019/005952, filed May 17, 2019, which claims priority to Korean Patent Application No. 10-2018-0057040 filed May 18, 2018.

INCORPORATION BY REFERENCE OF MATERIALS SUBMITTED ELECTRONICALLY

This application contains, as a separate part of the disclosure, a Sequence Listing in computer readable form (Filename: 56241_Seqlisting.txt; Size: 32,923 bytes; Created: Nov. 12, 2020), which is incorporated by reference in its entirety.

TECHNICAL FIELD

The present disclosure relates to a microneedle adhesive patch based on a hydrogel formulation.

BACKGROUND ART

Conventionally, a mechanical fixation means such as suture yarn and staples has been mainly used for suture of wounds that occur during surgical operations. However, when using the suture yarn and staples, tissue damage, inflammation, and necrosis may be caused due to strong and deep penetration thereof, a tension may be concentrated in a permeated area thereof and the suture yarn and staples need to be removed later. In order to overcome these problems and limitations, research on bio-adhesive materials is being conducted competitively.

Bio-adhesive material refers to a material that has adhesion properties to various biological threads such as cell wall, cell membrane, protein, DNA, growth factor, and tissue and may be used in a variety of medical applications including hemostatic agents, tissue adhesives, tissue fillers, tissue regeneration agents, drug delivery carriers, etc. However, conventionally developed medical bio-adhesive materials only serve as an aid to suture wounds that occur during surgical operations, and their functionality and physical properties are insufficient to be used independently in the actual medical field. Medical adhesive materials directly contact the tissue, and thus biocompatibility thereof is required. Further, the medical adhesive materials require the adhesion force such that the adhesion of the materials to the tissue may be instantly terminated in the body environment, and ease of use thereof. Further, a function thereof must be maintained for a long time in the body environment.

Representative bio-adhesive materials that have been commercialized and put into practice to date include cyanoacrylate-based instantaneous adhesives, fibrin glues, polyurethane-based adhesive patches, and the like. Cyanoacrylate cures without an initiator in a short time and has high adhesive strength. However, it is difficult to control the adhesion time of the cyanoacrylate during polymerization thereof. The cyanoacrylate lacks heat resistance and water resistance. The cyanoacrylate may produce bio-toxic byproducts. Since the fibrin-based bio-adhesive uses the actual blood coagulation process, it has relatively excellent biocompatibility and biodegradability. However, the adhesion force thereof is significantly lower than that of synthetic polymer-based adhesives, and thus its use is limited to areas requiring underwater adhesion. The polyurethane-based bioadhesive patches have high adhesion to tissues and flexibility. However, the tissue adhesion force thereof greatly drops in the presence of moisture, and the bio-toxicity of synthetic raw materials thereof should be removed. As such, most conventional adhesive materials are based on chemical synthesis, and they are weak to moisture and are toxic. Due to the lack of biodegradability thereof, use thereof in vivo is limited. Thus, the biosynthetic-based bio-adhesive material proposed as an alternative thereto is still largely insufficient in terms of adhesion in water and tissue adhesion force.

In a microneedle technology, a micro-sized channel that penetrates the skin layer is formed rather than the conventional simple patch form. The microneedle has been studied to develop a local and effective transdermal drug delivery system. The microneedle is to reduce the pain from the existing subcutaneous injection, and to overcome the drug degeneration and low absorption rate that occur during oral administration. The microneedle is mainly aimed at transdermal delivery of effective substances containing various drugs, hormones, vaccines, and the like. As a means to achieve this purpose, various materials such as silicon, metal, glass, and ceramic may be selected as the material of the microneedle. An effective substance may be injected into the skin layer by varying a form of the microneedle, for example, into solid, coated, dissolving, and hollow forms.

Hydrogel which is widely used in the field of tissue engineering means a material which swells by absorbing a large amount of water or body fluid into a cross-linked lattice thereof in water or body fluid, and which does not scatter in water and maintains a three-dimensional structure. Even after the swelling, the hydrogel is thermodynamically stable and has mechanical and physicochemical properties corresponding to an intermediate form between a liquid and a solid. These hydrogels may usually exhibit good biocompatibility, high porosity and oxygen permeability, and may exhibit similar physical properties to living soft tissues. The initial applications of the hydrogel based on natural and synthetic polymers were lenses and wound dressing means. In recent years, the range of the application thereof is expanding into the field of tissue engineering including hemostatic agents, tissue adhesives, drug delivery carriers, tissue fillers, tissue regeneration agents containing cells and growth factors.

Therefore, there is an urgent need to develop a new platform based adhesive material capable of improving the problems of the conventional adhesive patches including the cyanoacrylate-based instant adhesive, the fibrin glue and the polyurethane-based adhesive patch, and having excellent biocompatibility, biodegradability and bio-adhesion force, and capable of drug delivery to promote wound healing.

DISCLOSURE

Technical Problem

A purpose of the present disclosure is to overcome the technical limitations of the conventional adhesive patch, and to provide a microneedle patch capable of underwater adhesion and having improved biological tissue adhesion force, biocompatibility and biodegradability.

Further, a purpose of the present disclosure is to provide a microneedle patch capable of transdermally delivering drugs for promoting tissue regeneration and wound healing.

Technical Solution

The present inventors have identified that a mussel adhesive protein has adhesion ability in water, and has excellent biological tissue adhesion force and biocompatibility, and that the hydrogel may absorb water or body fluids and swell while maintaining a structure thereof in water. Based on this identification, the present disclosure has been completed.

Accordingly, the present disclosure provides a microneedle patch including a first hydrogel layer containing a mussel adhesive protein and hyaluronic acid, and a second hydrogel layer containing silk fibroin.

Further, the present disclosure provides a tissue adhesive including the microneedle patch according to the present disclosure.

Advantageous Effects

According to the present disclosure, the microneedle patch including the first hydrogel layer containing the mussel adhesive protein and the hyaluronic acid, and the second hydrogel layer containing the silk fibroin is provided. The tissue adhesion force thereof is excellent due to the first hydrogel layer containing the mussel adhesive protein.

Further, the microneedle patch according to the present disclosure has sufficient mechanical properties to penetrate to a stratum corneum, an epidermal layer, and a dermal layer. After the permeation, the first hydrogel layer swells rapidly by the water and/or body fluid, thereby inducing mechanical fixation of the microneedle, thus providing excellent skin adhesion and wound suturing effects.

The microneedle patch provided according to the present disclosure allows transdermal drug delivery without biotoxicity, and may be used to prevent inflammation, wound regeneration, and scar prevention or relief.

DESCRIPTION OF DRAWINGS

FIG. 1 is images before and after photo-crosslinking of a solution containing a mussel adhesive protein and hyaluronic acid, and silk fibroin solution as prepared according to Preparation Example 1.

FIG. 2 is a graph showing a maximum swelling ratio relative to a weight of each of gels resulting from drying hydrogels of various compositions prepared according to Preparation Example 1 and immersing the same in physiological saline and drying the same. The compositions of hydrogels (a) to (f) are as follows: (a) 70% by weight of SF (silk fibroin), 1 mM Ru(II)bpy$_3^{2+}$, 30 mM peroxide sulfate as dissolved in distilled water; (b) 40% by weight fp-151, 5% by weight HA (hyaluronic acid), 1 mM Ru(II)bpy$_3^{2+}$, 40 mM peroxide sulfate as dissolved in distilled water; (c) 40% by weight fp-151, 10% by weight HA, 1 mM Ru(II)bpy$_3^{2+}$, 40 mM peroxide sulfate as dissolved in distilled water; (d) 40% by weight fp-151, 10% by weight HA, 1 mM Ru(II)bpy$_3^{2+}$, 30 mM peroxide sulfate as dissolved in distilled water; (e) 35% by weight fp-151, 15% by weight HA, 1 mM Ru(II)bpy$_3^{2+}$, 30 mM peroxide sulfate as dissolved in distilled water; and (f) 35% by weight fp-151, 15% by weight HA, 1 mM Ru(II)bpy$_3^{2+}$, 30 mM peroxide sulfate as dissolved in physiological saline.

FIG. 3 is a graph showing the result of identifying cytotoxicity by performing a contact experiment using a photo-crosslinked hydrogel eluate prepared according to Preparation Example 1.

FIG. 4 is a picture of a vacuum chamber having a backside vacuum system according to Preparation Example 2 and a drawing of a silicone mold.

FIG. 5 is a picture of a single-layer microneedle patch based on a hydrogel formulation containing the mussel adhesive protein prepared according to Example 1-1.

FIG. 6 shows an optical microscope image, a fluorescence microscope image and a combination thereof of a double-layer microneedle patch prepared according to Example 1-2 based on an injection time (10 to 120 minutes) of a first photo-crosslinking solution containing the mussel adhesive protein into a mold.

FIG. 7 is a photograph of each needle based on an elapsed time when double-layer microneedle patches with different ratios of swellable/non-swellable hydrogels are immersed in physiological saline according to Experimental Example 3.

FIG. 8 is a graph showing a fracture force of each of a single-layer microneedle containing the mussel adhesive protein and a double-layer microneedle containing both the mussel adhesive protein and the silk fibroin, and a graph comparing the single-layer and the double-layer microneedle in terms of the fracture force and a force required to penetrate the skin tissue, via a compression mode experiment using Instron according to Experimental Example 4-1.

FIG. 9 is a picture of the result of identifying a permeation rate with a tissue staining drug after a swellable single-layer microneedle patch containing the mussel adhesive protein is permeated into rat skin tissue using a thumb according to Experimental Example 4-2.

FIG. 10 is a graph showing the change in the tissue adhesion force based on a content of a swellable hydrogel of a double-layer microneedle patch containing the mussel adhesive protein and silk fibroin according to Experimental Example 5-1.

FIG. 11 is a graph comparing tissue adhesion forces of the commercialized adhesive tape for wound suture and a double-layer microneedle patch containing the mussel adhesive protein and the silk fibroin onto a semi-dry surface or a wet surface via an Instron experiment using pig skin according to Experimental Example 5-2.

FIG. 12 is a photograph showing the application of a double-layer microneedle patch containing the mussel adhesive protein and the commercially available adhesive tape for wound suture onto a 3 cm long wound of the rat skin tissue according to Experimental Example 6.

FIG. 13 shows an image that FITC-dextran is loaded on a single-layer microneedle patch based on a hydrogel formulation containing the mussel adhesive protein according to Experimental Example 7 and a graph showing the degree of FITC-dextran release when immersing the patch in physiological saline or physiological saline containing 0.02 mg/L trypsin.

MODES OF THE INVENTION

The present disclosure relates to a microneedle patch including a first hydrogel layer containing a mussel adhesive protein and hyaluronic acid, and a second hydrogel layer containing silk fibroin.

In the present disclosure, the mussel adhesive protein is an adhesive protein derived from mussel, and, preferably includes a mussel adhesive protein derived from *Mytilus edulis, Mytilus galloprovincialis* or *Mytilus coruscus*, or a variant thereof but is not limited thereto.

The mussel adhesion proteins according to the present disclosure may include Mefp (*Mytilus edulis* foot protein)-1, Mgfp (*Mytilus galloprovincialis* foot protein)-1, Mcfp (*Mytilus coruscus* foot protein)-1, Mefp-2, Mefp-3, Mgfp-3 and Mgfp-5 as derived from the above mussel species, or a variant thereof. Preferably, the mussel adhesion proteins according to the present disclosure may include a fusion protein to which one protein or two or more proteins selected from a group consisting of fp (foot protein)-1 (SEQ ID NO: 1), fp-2 (SEQ ID NO: 4), fp-3 (SEQ ID NO: 5), fp-4 (SEQ ID NO: 6), fp-5 (SEQ ID NO: 7), and fp-6 (SEQ ID NO: 8) are linked, or a variant of the protein but is not limited thereto.

Further, the mussel adhesive protein according to the present disclosure contains all of the mussel adhesive proteins described in International Publication No. WO2006/107183 or WO2005/092920. Preferably, the mussel adhesive protein may include a fusion protein such as fp-151 (SEQ ID NO: 9), fp-131 (SEQ ID NO: 10), fp-353 (SEQ ID NO: 11), fp-153 (SEQ ID NO: 12), and fp-351 (SEQ ID NO: 13), but is not limited thereto. Further, the mussel adhesive protein according to the present disclosure may include a polypeptide in which 1 to 12 or greater decapeptides (SEQ ID NO: 2) as repeated about 80 times in fp-1 are continuously linked to each other.

Further, the mussel adhesive protein according to the present disclosure may include a polypeptide in which 1 to 12 or greater decapeptides (SEQ ID NO: 2) as repeated about 80 times in fp-1 are continuously linked to each other. Preferably, the mussel adhesive protein according to the present disclosure may include fp-1 variant polypeptide (SEQ ID NO: 3) in which 12 decapeptides (SEQ ID NO: 2) are continuously linked to each other, but is not limited thereto.

Further, the mussel adhesive protein according to the present disclosure may be a variant (SEQ ID NO: 15) of fp-151, but is not limited thereto. The protein sequence represented by SEQ ID NO: 15 is a sequence free of a linker sequence and the like compared to SEQ ID NO: 9. Specifically, the protein sequence represented by SEQ ID NO: 15 is a fusion protein sequence in which the sequence of mgfp-5 represented by SEQ ID NO: 16 is fused to between the fp-1 variant sequences represented by SEQ ID NO: 14.

In a preferred aspect of the present disclosure, the mussel adhesive protein according to the present disclosure includes the amino acid sequence represented by SEQ ID NO: 9 or SEQ ID NO: 15.

According to the present disclosure, the mussel adhesive proteins may be modified within a range containing conservative amino acid sequences that may maintain the properties of the mussel adhesive proteins as mentioned above. That is, amino acid sequences having a sequence identity of 70% or more, preferably 80% or more, even more preferably 90% or more, that is, 95%, 96%, 97%, 98% 99% or more with the amino acid sequence represented by the SEQ ID NOs as mentioned above and exhibiting a substantially equivalent effect thereto may also be included within the scope of the present disclosure.

After insertion of the needle composed of the mussel adhesive protein and hyaluronic acid into the tissue, the needle rapidly absorbs body fluid and swells, thereby inducing mechanical fixation between the inserted needle and surrounding tissue, thereby improving the tissue adhesion force of the microneedle patch. In addition, the non-swellable layer based on the silk fibroin used in the microneedle patch according to the present disclosure may have the inherent strong mechanical properties of the silk fibroin and may hardly swell due to the hard photo-crosslinking. Thus, after the needle is inserted into the tissue, the non-swellable layer may prevent the microneedle patch from detaching due to swelling at the boundary between the tissue and the patch. The separation between the swellable layer and the non-swellable layer may be prevented via the photo-crosslinking thereof with the amino acids of the mussel adhesive protein in the swellable layer.

After the first hydrogel layer penetrates the tissue, it may rapidly absorb water or body fluid and swell. The second hydrogel layer hardly swells due to the strong mechanical properties and the crosslinking of the silk fibroin, thereby to prevent the separation of the microneedle patch from the tissue, which may otherwise be caused when the microneedle part rapidly swells after penetrating the tissue.

The first hydrogel layer is located at the tip end of the microneedle based on the microneedle, and the second hydrogel layer is located on the first hydrogel layer.

In the microneedle patch according to the present disclosure, the first and second hydrogel layers may be crosslinked with each other. The crosslinked first and second hydrogel layers may have a three-dimensional network structure formed via crosslinking between tyrosine residues contained in the mussel adhesive protein. Crosslinking the first and second hydrogel layers may have following advantages: when the first hydrogel layer penetrates the tissue and then rapidly swells by absorbing body fluid, the first hydrogel layer may not be separated from the second hydrogel layer. In this connection, the first and second hydrogel layers may be photo-crosslinked with each other. In this case, the photo-crosslinking may be performed using visible light, and the visible light may have a wavelength of 420 to 480 nm, preferably, 449 to 455 nm, more preferably about 452 nm.

In the microneedle patch according to the present disclosure, the mussel adhesive protein may be contained in 25 to 50% (w/v) with respect to the first hydrogel layer. When the mussel adhesive protein content is lower than 25% (w/v), the mechanical strength required for skin penetration may not be secured because the microneedle is formed in a thin and incomplete shape. When the mussel adhesive protein content is higher than 50% (w/v), the viscosity of the solution containing the mussel adhesive protein is high, thus making it difficult for the solution to inject into a microneedle mold. When preparing the microneedle in this state, a problem arises in that an incomplete microneedle is formed.

In the microneedle patch according to the present disclosure, the hyaluronic acid may have an average molecular weight of 40 kDa to 150 kDa. Hyaluronic acid is a bio-derived polymer material in which N-acetyl-D-glucosamine and D-glucuronic acid are alternately linked to each other in a chain form. The hyaluronic acid is richly present in animal tissues such as skin and umbilical cord, and is suitable as a biomaterial and physical properties thereof may be easily controlled. When the average molecular weight of the hyaluronic acid is lower than 40 kDa, the degree of crosslinking increases because of the high flexibility of the chain, so that the swellability of the first hydrogel layer containing the hyaluronic acid decreases. When the average molecular weight of hyaluronic acid is higher than 150 kDa, the viscosity of the hyaluronic acid-containing solution is high, making it difficult for the solution to inject into the microneedle mold, resulting in a problem that an incomplete microneedle is formed.

In the microneedle patch according to the present disclosure, the hyaluronic acid may be contained in an amount of 5 to 20% (w/v) with respect to the first hydrogel layer. When the content of hyaluronic acid is lower than 5% (w/v), there is a problem in that the swellability of the first hydrogel layer is lowered. When the hyaluronic acid content is higher than 20% (w/v), the first hydrogel layer contains relatively little mussel adhesive protein, resulting in a problem in that sufficient crosslinking does not occur due to a lack of tyrosine residues. Preferably, the hyaluronic acid and the mussel adhesive protein may be contained in a weight ratio of 2:8 to 3:7. This induces coacervate formation via ionic bonding between hyaluronic acid and mussel adhesive protein. Thus, using the very low surface tension properties of the coacervate, the solution based on the mussel adhesive protein having the high surface adhesion force and viscosity may be easily injected into the microneedle mold. Further, using the characteristics of the coacervate that is not mixed with water and exists in a liquid state, a double-layer microneedle patch may be prepared without mixing the solution with the silk fibroin-based solution for the second layer as injected when preparing the double-layer microneedle patch.

In the microneedle patch according to the present disclosure, the silk fibroin may be contained in an amount of 40 to 70% (w/v) with respect to the second hydrogel layer. When the content of silk fibroin is lower than 40% (w/v), the mechanical strength required for skin penetration may not be secured because the microneedle is formed in a thin and incomplete form. When the content of silk fibroin is higher than 70% (w/v), the viscosity of the solution containing the silk fibroin is high, thus making it difficult for the solution to inject into the mold using a pipette. Preferably, the silk fibroin may be contained in an amount of 55 to 70% (w/v) with respect to the second hydrogel layer.

In the microneedle patch according to the present disclosure, the first hydrogel and the second hydrogel may have a thickness ratio of 2:8 to 8:2. When the thickness ratio of the first hydrogel to the second hydrogel is lower than 2:8, the effect of mechanical fixation on the tissue decreases rapidly due to the decrease in the content of the swellable portion after penetration of the needle into the tissue. When the thickness ratio is higher than 8:2, the microneedle part and the patch part may be separated from each other while a lower portion of the microneedle part including the bottom face of the microneedle part severely swells after the penetration into the tissue. In order to induce effective tissue adhesion via sufficient swelling of the first hydrogel, the thickness of the first hydrogel may amount to 40 to 70%, preferably 55 to 65%, based on the total thickness of the microneedle.

Further, the present disclosure relates to a tissue adhesive including the microneedle patch according to the present disclosure. The tissue adhesive according to the present disclosure is applied locally to the living body and may replace the suture yarn for surgical operation and be easily and immediately adhered to the wound site for suturing the wound. In the present specification, the terms "living tissue" and "tissue" include, but are not limited to, tissues of skin, nerves, brain, lung, liver, kidney, stomach, small intestine, and rectum.

The bio-adhesive material according to the present disclosure is preferably in a form of a microneedle patch based on a dried gel formulation. The dried gel form may be induced via a photo-crosslinking reaction. Rapid swelling thereof is possible via body fluid absorption after the insertion into the tissue. Further, as time goes by, the gel-like protein is gradually biodegraded and does not require a separate removal process thereof after suturing which is otherwise required when using the suture yarn or the staple. Further, the microneedle patch containing drugs such as anti-inflammatory drugs may allow direct transdermal drug delivery via insertion to the tissue and gel decomposition, and thus may be used for the purpose of preventing inflammation, of effective wound regeneration, and of preventing or alleviating scars. The drug is not specifically limited, and may include protein medicines, peptides, anti-inflammatory drugs, and the like.

In addition, the present disclosure provides a preparation method for preparing the bio-adhesive material according to the present disclosure with excellent wound suturing and regeneration effects.

More specifically, the present disclosure provides a method of preparing a bio-adhesive material in a form of a microneedle patch including a swellable hydrogel layer containing the mussel adhesive protein and hyaluronic acid and a non-swellable hydrogel layer containing silk fibroin.

In the present disclosure, in order to provide a bio-adhesive material of a microneedle patch type based on a hydrogel formulation containing the mussel adhesive protein for wound suture and regeneration, the method may include inducing a photo-crosslinking reaction using a fluorescent lamp. That is, the present disclosure provides a preparation method of a bio-adhesive material, the method including adding a solution containing a photoreactive metal ligand and an electron acceptor to a solution containing a protein, and inducing a photo-crosslinking reaction via light irradiation under a fluorescent lamp including blue light.

The mussel adhesive protein-based photo-crosslinkable bio-adhesive material prepared by such a preparation method may be in the form of a gel having a three-dimensional network structure as formed via crosslinking between tyrosine residues contained in the mussel adhesive protein.

In the present disclosure, the photoreactive metal ligands for providing molecules that strongly absorb visible light may include one or more selected from a group consisting of ruthenium (Ru (II)), palladium (Pd (II)), copper (Cu (II)), nickel (Ni (II)), manganese (Mn (II)), and iron (Fe (III)). For example, the photoreactive metal ligand may be [Ru(II) bpy$_3$]Cl$_2$, but is not limited thereto.

In addition, a material for providing an electron acceptor may include at least one selected from a group consisting of sodium persulfate, periodate, perbromate, perchlorate, vitamin (B12), pentaaminechlorocobalt (III), ammonium cerium (IV) nitrate, oxalic acid, and EDTA. For example, the material may be preferably sodium persulfate, but is not limited thereto.

More preferably, Ru(II)bpy$^{2+}$ and sodium persulfate solution are added to the solution in which the mussel adhesive protein or silk fibroin protein is dissolved. When a fluorescent lamp including light in a wavelength range of 420 to 480 nm irradiates light to the mixture solution, a gel-like bio-adhesive material having a three-dimensional network structure may be formed.

In the present disclosure, in order to prepare a microneedle patch type bio-adhesive material based on a hydrogel formulation containing the mussel adhesive protein for wound suturing and regeneration, a backside vacuum chamber may be preferably used. The present disclosure provides a preparation method of a bio-adhesive material, the method including loading a photo-crosslinkable protein solution on a mold for microneedle patch production on the backside vacuum chamber to induce a backside vacuum, and injecting the solution into the mold using the backside vacuum.

The backside vacuum chamber is devised because it is difficult for the mussel adhesive protein solution with high surface adhesion force and viscosity to be applied to the vacuum chamber and centrifugation as conventionally used for the fabrication of the microneedle patch. Inducing only the backside vacuum may allow manufacturing a normal shaped microneedle patch via easy and quick injection of the protein solution into the mold, and further allow preventing the formation of bubbles in the microneedle that otherwise occur when using the conventional vacuum chamber. When the backside vacuum chamber is used, a time duration taken for the solution injection into the mold for the microneedle patch production, photo-crosslinking, and sufficient drying may be about 12 to 20 hours, preferably 14 to 16 hours, but may be properly adjusted according to the amount of the solution placed on the mold.

In addition, in accordance with the present disclosure, an adhesion or bonding method of the microneedle patch type bio-adhesive material to a tissue is provided which includes topically applying the microneedle patch type bio-adhesive material based on a hydrogel formulation containing the mussel adhesive protein for wound suture and regeneration onto the individual's transdermal.

In the present disclosure, the individual may be a mammal, for example, a human, cow, horse, pig, dog, sheep, goat, or cat.

Further, the present disclosure provides a method of treating a wound of a patient, the method including contacting the microneedle patch with the wound site of the patient, in which the microneedle patch includes a first hydrogel layer containing the mussel adhesive protein and hyaluronic acid; and a second hydrogel layer containing silk fibroin.

The term "treatment" as used herein may refer to provide healing of the wound in a shorter time compared to natural healing. The treatment may include improvement and/or alleviation of the wound. Further, the treatment may include all of the treatments of wounds and/or wound-related diseases. The treatment may mean healing and/or regeneration of damaged tissue caused by the wound. The wound treatment may include the skin regeneration. Further, the treatment may be to recover and maintain an original composition of the damaged tissue. Further, the treatment may be to promote healing and/or regeneration of the damaged tissue while minimizing complications of diseases and/or scars related to wounds.

The wound site tissue may generally include any tissue in which one or more microneedles of the microneedle patch may at least partially penetrate. Non-limiting examples of tissues having surfaces that may be in contact with the plurality of microneedles include skin, eyes (e.g., cornea, conjunctiva), gastrointestinal tract (e.g., mouth, esophagus, stomach, small and large intestine, rectum and anus), a tissue inside the nose, the vagina, a tissue inside the ear (for example, the eardrum), muscles, blood vessels, cell membranes, or a combination thereof. The tissue may be a mammalian bio-tissue such as mammalian skin.

In the present disclosure, the microneedle patch may contain the mussel adhesive protein and hyaluronic acid in a "therapeutically effective amount", which represents the amount of active ingredients according to the present disclosure that is effective for treating wounds. That is, the therapeutically effective amount may mean an appropriate amount to sufficiently prevent serious side effects within the scope of medical judgment while being very sufficient to achieve the desired effect. The amount of the microneedle patch according to the present disclosure as applied may be appropriately adjusted in consideration of the route of administration and the administration subject.

Further, the present disclosure provides a microneedle patch for use in wound healing, in which the microneedle patch includes a first hydrogel layer containing a mussel adhesive protein and hyaluronic acid; and a second hydrogel layer containing silk fibroin.

Further, the present disclosure provides the use of the microneedle patch in the preparation of a kit for wound treatment, in which the microneedle patch includes a first hydrogel layer containing a mussel adhesive protein and hyaluronic acid; and a second hydrogel layer containing silk fibroin.

EXAMPLES

Hereinafter, the present disclosure will be described in more detail based on Preparation Examples and Examples. However, the following examples are only provided for easier understanding of the present disclosure, and the scope of the present disclosure is not limited to the examples.

Preparation Example 1. Preparation of Hydrogel Containing Mussel Adhesive Protein and Hydrogel Containing Silk Fibroin Preparation Example 1-1. Production of Recombinant Mussel Adhesive Protein fp-151

We synthesized an fp-1 variant composed of 6 decapeptides so that decapeptide composed of 10 amino acids as repeated 80 times in a mussel adhesive protein fp-1 existing in nature may be expressed in *E. coli*. We inserted a gene of Mgfp-5 (Genbank No. AAS00463 or AY521220) into between the two fp-1 variants. Thus, the decapeptide was successfully expressed in *E. coli*. Thereafter, mussel adhesive protein fp-151 was produced via a simple purification and separation process using acetic acid (see D. S. Hwang et. al., Biomaterials 28, 3560-3568, 2007). Specifically, the fp-1 variant (hereinafter, referred to as 6×AKPSYPPTYK) represented by SEQ ID NO: 14 in which 6 peptides, each composed of AKPSYPPTYK represented by SEQ ID NO: 2 in the amino acid sequence of fp-1 (Genbank No. Q27409 or S23760) are repeatedly linked to each other was prepared. We appropriately combined the 6×AKPSYPPTYK with the N-terminus of mgfp-5 represented by SEQ ID NO: 16 and appropriately combined 6×AKPSYPPTYK with the C-terminus of mgfp-5. Thus, the mussel adhesive protein fp-151 represented by SEQ ID NO: 9 was prepared.

Preparation Example 1-2. Preparation of Hydrogel Containing Mussel Adhesive Protein and Hyaluronic Acid 30 to 35% by weight of mussel adhesive protein produced via Preparation Example 1-1 and 5 to 20% by weight of hyaluronic acid powder having an average molecular weight of 100 kDa were added to distilled water or physiological saline, and then mixed. Then, 1 mM tris bipyridine ruthenium dichloride and 20 to 40 mM sodium persulfate solution were added thereto, and then the mixture was exposed, for 16 to 20 hours, to natural light including light from a fluorescent lamp to obtain a dried hydrogel.

FIG. 1 shows, at a left thereof, pictures before and after photo-crosslinking of the hydrogel containing the mussel adhesive protein and hyaluronic acid. After photo-crosslinking, the hydrogel turned yellow due to the addition of ruthenium ions.

Preparation Example 1-3. Production of Silk Fibroin

After boiling 8 L of distilled water in which 0.75 g of sodium oleate and 0.45 g of sodium carbonate were dissolved, 150 g of clean cocoon was added thereto. Then, the mixture solution was boiled for about 40 minutes. This process was repeated twice to remove sericin from the cocoon. The salt of the cocoon from which sericin was removed was removed using boiling water and the cocoon was dried completely. Using a distillation machine, we boiled a solution with a molar ratio of 1:8:2 of calcium chloride:distilled water:100% ethanol to 100° C., and then put the refined cotton thereto at a ratio of 1:20. Then, random cleavage thereof was conducted for about 20 hours at 98 to 100° C. The silk fibroin solution was filtered using Miracloth, followed by dialysis and freeze-drying to obtain purified silk fibroin powders.

Preparation Example 1-4. Preparation of Hydrogel Containing Silk Fibroin

We added 70% by weight of silk fibroin protein as produced via Preparation Example 1-3 to distilled water. Then, after adding 1 mM tris bipyridine ruthenium dichloride and 30 mM sodium persulfate solution thereto, the mixture solution was exposed, for 16 to 20 hours, to natural light including light from a fluorescent lamp to obtain a dried hydrogel.

The pictures before and after photo-crosslinking of the hydrogel containing the silk fibroin protein are shown on the right side of FIG. 1. After the photo-crosslinking, the hydrogel turned yellow due to the addition of ruthenium ions.

Experimental Example 1. Identification of Swelling Ratio of Hydrogels Prepared According to Preparation Examples 1-3 and 1-4

The hydrogels prepared according to Preparation Examples 1-3 and 1-4 were completely dried to identify the swelling ratio of the hydrogels. After measuring the weight of the dried hydrogel, we immersed the same in a physiological saline. Then, the swelling ratio thereof was identified via measuring the weight of the swollen hydrogel compared to the weight of the dried hydrogel. The swelling ratio at a time point when the swelling ratio does not change over time was designated as the equilibrium swelling ratio. The equilibrium swelling ratio of the hydrogel of each of the various components and concentrations was measured and shown in FIG. 2.

As a result, it was identified that in all experimental conditions, when using less than 30 mM peroxide sulfate, the gel was not formed under natural light including light from a fluorescent lamp. Further, the hydrogel obtained under the condition of 35% by weight of fp-151, 15% by weight of HA, 1 mM Ru(II)bpy$_3^{2+}$, 30 mM peroxide sulfate as dissolved in physiological saline exhibited the highest swelling ratio. The hydrogel obtained when 70% by weight of SF was used was substantially not swollen.

Experimental Example 2. Identification of Cytotoxicity of Hydrogels Prepared According to Preparation Examples 1-3 and 1-4

We mixed 1 mM Ru(II)bpy$_3^{2+}$ and 30 mM peroxide sulfate with each of a solution containing 35% by weight of fp-151 and 15% by weight of HA and a solution of 70% by weight of silk fibroin. The hydrogel was crosslinked under natural light including light from the fluorescent lamp and was immersed in a cell medium at an elution ratio of 0.1 g/L according to ISO 10993-5 and eluted at 37° C. for 24 hours. This eluate was applied to a single-layer of HaCaT keratinocytes and NIH3T3 fibroblasts. Then, the effect thereof on cell growth for 72 hours was identified using cck-8 solution and based on an OD value of 450 nm. A group subjected to no treatment and a group treated with 15% DMSO solution were used as controls.

As a result, neither the hydrogel containing the mussel adhesive protein and hyaluronic acid nor the hydrogel containing silk fibroin exhibited cytotoxicity against the keratinocytes and fibroblasts (FIG. 3).

Preparation Example 2. Manufacturing of Vacuum Chamber and Mold for Microneedle Patch Preparation When the vacuum chamber and centrifugation which are mainly used for manufacturing the conventional microneedle patch is applied to a high concentration of mussel adhesive protein solution with high adhesion force and viscosity, air bubbles are generated during the injection process of the solution into the mold or the solution is dried before completely filling the mold.

Accordingly, a backside vacuum chamber was manufactured in which vacuum was applied only in a downward direction of the mold. A staircase having a hole defined inwardly was formed in an area where a mold on a lid will be placed, so that an entire face of a PDMS mold for microneedle patch production was held under vacuum. Further, a copper mesh was inserted in the staircase to prevent the mold for microneedle patch production from bending (FIG. 4).

Using grayscale lithography technology, an SU-8 master mold in which conical microneedles (each having diameter 250 μm, and height 750 μm) are arranged in a 10×10 matrix and are spaced from each other by 500 μm. A PDMS solution was poured into the master mold to obtain a mold for the microneedle patch production.

Example 1. Microneedle Patch Preparation

Example 1-1. Preparation of Single-Layer Microneedle Patch Based on Hydrogel Formulation Containing Mussel Adhesive Protein and Hyaluronic Acid 50 μl of physiological saline containing 35% by weight of fp-151, 15% by weight of HA, 1 mM Ru(II)bpy$_3^{2+}$, and 30 mM peroxide sulfate was placed on the microneedle mold prepared in Preparation Example 2, and then −80 kPa of vacuum was created. The protein solution was injected into the microneedle mold due to vacuum, and at the same time, photo-crosslinking thereof occurred under natural light including light from the fluorescent lamp. After about 16 to 20 hours, the vacuum was removed, and then the mold and the produced protein-based microneedle patch were separated from each other using a transparent adhesive tape. FIG. 5 shows the mussel adhesive protein-based single-layer microneedle patch as thus produced.

Example 1-2. Preparation of Double-Layer Microneedle Patch Containing Hydrogel Layer Containing Mussel Adhesive Protein and Hydrogel Layer Containing Silk Fibroin A first photo-crosslinking solution (30 μl of physiological saline containing 35% by weight fp-151, and 15% by weight HA) containing the mussel adhesive protein was placed on the mold under a backside vacuum condition created using the chamber according to Preparation Example 2. The solution was injected into the mold for 10 minutes to 2 hours, and then the remaining solution on the surface was scraped off. Immediately, a second photo-crosslinking solution (40 μl of distilled water containing 70% by weight of SF, 1 mM Ru(II)bpy$_3^{2+}$, 30 mM peroxide sulfate, and 1 mg/ml rhodamine B) containing silk fibroin was placed on the mold. The solution was injected into the mold for 16 to 20 hours. Then, the vacuum was removed and the microneedle patch was separated from the mold using a transparent adhesive tape.

To distinguish the two hydrogel layers from each other, we mixed rhodamine B staining solution with silk fibroin solution. A patch was prepared. The resulting double-layer microneedle patch was identified via an optical microscope and a fluorescence microscope, and an image thereof is shown in FIG. 6. It was identified that the ratio of the swellable portion (first hydrogel layer)/non-swellable portion (second hydrogel layer) of the microneedle patch may be adjusted by controlling the injection time of the first photo-crosslinking solution.

Experimental Example 3. Identification of Swelling of Microneedle Patch Based on Hydrogel Ratio To identify the swelling of each of the double-layer microneedle patches with different ratios of swellable/non-swellable portions as prepared according to Example 1-2, the microneedle patch was immersed in the physiological saline. Then, we identified the swelling with an optical microscope at regular intervals and the result is shown in FIG. 7.

As shown in FIG. 7, it was identified that the overall swelling ratio of the microneedle increases as a percentage of the swellable portion increases. It was identified that when the percentage of the swellable portion is 80%, a lower portion of the needle was severely swollen and the swellable portion was separated from the non-swellable portion. Therefore, in the subsequent experiments except for the adhesion test, the double-layer microneedle patch with a percentage of the swellable portion of 60% which swells most stably without separation of the swellable portion from the non-swellable portion was used.

Experimental Example 4. Identification of Skin Penetration and Swelling of Microneedle Patch Experimental Example 4-1. Fracture Force Identification Experiment Instron was used to identify the fracture force of each needle of the single-layer or the double-layer microneedle patch as prepared according to Example 1. The fracture force at which the needle breaks when compressing the microneedle patch fixed to a floor using an Instron at a constant speed of 1.2 mm/min was identified (FIG. 8).

As a result, it was identified that both the single-layer microneedle patch containing the mussel adhesive protein as well as the double-layer microneedle patch including the silk fibroin had sufficient force more than a force (0.05 N/needle) as required to penetrate the skin tissue. Further, it was identified that the fracture force of the double-layer microneedle increased by more than about 4.5 times due to silk fibroin having excellent mechanical properties.

Experimental Example 4-2. Identification Experiment of Microneedle Penetration Rate into Skin Tissue We gently pressed a patch composed of single-layer microneedles containing the mussel adhesive protein prepared according to Example 1-1 in a 10×10 matrix on rat skin tissue for 5 minutes with a thumb. The permeation rate was identified via measuring the number of microneedles as permeated via the tissue staining drug (FIG. 9).

As a result, it was identified that even the single-layer microneedle which had a relatively low fracture force could penetrate the rat skin tissue without breaking a single needle.

Experimental Example 5. Experiment to Identify Tissue Adhesion Force of Microneedle Patch Experimental Example 5-1. Comparative Experiment of Tissue Adhesion Force of Double-Layer Microneedle Patch Based on Percentage of Swellable Portion We attached a pig skin to a bottom face of an aluminum rod (1.4 cm in diameter) with instant adhesive. The rod was connected to the Instron instrument sensor. Each of the microneedle patches prepared according to Example 1 (using percentage of swellable portion of 20, 40, 60 and 80%) was attached on a top face of the aluminum rod using double-sided tapes. The microneedle patch was pressed against the underlying pig skin at a constant rate of 100 mm/min so that a final force was 30 N/patch and, after 10 minutes, was removed therefrom at a rate of 2 mm/min. At this time, the value obtained by dividing the highest force by an area was defined as the tissue adhesion force, which is shown on a graph (FIG. 10).

The double-layer microneedle patch with a percentage of the swellable portion of 60% had the highest tissue adhesion force due to mechanical fixation and bonding with surrounding tissues via swelling. It was identified that in the double-layer microneedle patch with a percentage of the swellable portion of 80%, the swellable layer was separated from the non-swellable layer and the patch, and thus the tissue adhesion force decreased.

Experimental Example 5-2. Comparative Experiment of Tissue Adhesion Forces of Present Microneedle Patches and Commercially Available Adhesive Tape We attached a pig skin to a bottom face of an aluminum rod (1.4 cm in diameter) with instant adhesive. The rod was connected to the Instron instrument sensor. Each of the microneedle patches prepared according to Example 1 (percentage of swellable portion of 60%) and a commercialized adhesive tape for wound suture (3M Steri-Strip™) was attached on a top face of the aluminum rod using double-sided tapes. The microneedle patch or the commercialized adhesive tape was pressed against the underlying pig skin at a constant rate of 100 mm/min so that a final force was 30 N/patch and, after 2 minutes, was removed therefrom at a rate of 2 mm/min. At this time, the value obtained by dividing the highest force by an area was defined as the tissue adhesion force, which is shown on a graph (FIG. 11). The pig skin surface condition as used in the experiment was as follows: for a semi-dry state, water on the skin surface was lightly wiped with a paper tissue, and was used in the experiment; and for a wet state, 100 μl of physiological saline was sprayed on the surface which in turn was used in the experiment immediately.

The double-layer microneedle patch based on a hydrogel formulation containing the mussel adhesive protein exhibited excellent tissue adhesion force (134.7±27.7 kPa) comparable to the commercial adhesive tape (122.3±29.1 kPa) in the semi-dry surface condition. In the wet surface condition, the double-layer microneedle patch based on a hydrogel formulation containing the mussel adhesive protein exhibited the tissue adhesion force (123.3±21.1 kPa) as similar to that in the dry surface condition. However, in the wet surface condition, the commercial adhesive tape lost the tissue adhesion force.

Experimental Example 6. Identification of Wound Suture Effect of Microneedle Patch We induced a wound of sufficient length (3 cm) such that the wound is able to be opened toward both sides of the wound on the rat skin tissue where the hair is not completely removed. We lightly pressed the double-layer microneedle patch prepared according to Example 1 in the form of a strip (percentage of the swellable portion of 60%, 1×4 cm$^2$) against the wound using a thumb. The commercially available adhesive tape for wound suture (3M Steri-Strip™) as a control was applied on the wound according to an attachment manual thereof. We compared and identified the possibility of suturing the wound (FIG. 12).

The commercially available medical adhesive tape was not firmly fixed to the tissue and was opened while the wound was opened, and could not absorb blood. Thus, as the blood was collected, it was easily detached therefrom. To the contrary, the microneedle patch as prepared according to Example 1 easily sutured a 3 cm long wound. After the suturing, as the blood was collected in the wound, the patch absorbed the blood and maintained the sutured state without lifting up the patch.

Experimental Example 7. Identification of Substance Delivery Effect of Microneedle Patch FITC-dextran (77 kDa) per microneedle patch was mounted on a photo-crosslinkable mussel adhesive protein aqueous solution such that a final concentration was 5 mg/ml. Then, using a backside vacuum system, a microneedle patch based on a hydrogel formulation having the FITC-dextran mounted thereon was prepared. The microneedle patch was immersed in physiological saline at 37° C. or physiological saline having 0.02 mg/L trypsin added thereto, and then samples were collected every certain period, and quantified using a fluorescence spectrometer. The release rate and amount of the mounted fluorescent substance as released via the diffusion phenomenon due to the swelling of the hydrogel were identified. For the quantification of the fluorescent substance, a standard curve representing the fluorescence value based on the concentration of FITC-dextran was used (FIG. 13).

It was identified that in the physiological saline to which 0.02 mg/L trypsin was added, the protein-based microneedle patch was degraded within two days, and an entirety of the loaded FITC-dextran was released. It was identified that in the physiological saline without enzyme, about 35% of the loaded FITC-dextran was released for one week. This indicates that due to the diffusion phenomenon via swelling of the hydrogel formulation in a photo-crosslinked state, the release rate and amount of the mounted fluorescent substance as released may be controlled based on the degree of photo-crosslinking. This means that the microneedle patch containing the mussel adhesive protein may be applied to a drug delivery system.

As described above, the present disclosure has been described based on the examples. A person skilled in the art to which the present disclosure belongs will be able to understand that the present disclosure may be implemented in other concrete forms without changing the technical idea or essential features. Therefore, the above-described examples are illustrative in all respects and should be understood as non-limiting. The scope of the present disclosure is indicated by the claims to be described later rather than by a detailed description. All changes or modifications derived from the meaning and scope of the claims and equivalent concepts should be interpreted as being contained in the scope of the present disclosure.

The invention claimed is:

1. A microneedle patch comprising:
   a first hydrogel layer containing a mussel adhesive protein and hyaluronic acid; and
   a second hydrogel layer containing silk fibroin,
   wherein the mussel adhesive protein is crosslinked by covalent bonds, and
   wherein the weight ratio of the hyaluronic acid to the mussel adhesive protein ranges from 2:8 to 3:7.

2. The microneedle patch of claim 1, wherein the mussel adhesive protein includes: a protein having an amino acid sequence selected from the group consisting of SEQ ID NO: 1, SEQ ID NO: 4, SEQ ID NO: 5, SEQ ID NO: 6, SEQ ID NO: 7 and SEQ ID NO: 8; or a fusion protein having the amino acid sequence of SEQ ID NO: 9.

3. The microneedle patch of claim 1, wherein the first hydrogel layer and the second hydrogel layer are crosslinked with each other.

4. The microneedle patch of claim 1, wherein a content of the mussel adhesive protein is in a range of 25 to 50% (w/v) based on the first hydrogel layer, where the first hydrogel layer is a dried hydrogel layer.

5. The microneedle patch of claim 1, wherein the hyaluronic acid has an average molecular weight of 40 kDa to 150 kDa.

6. The microneedle patch of claim 1, wherein a content of the hyaluronic acid is in a range of 5 to 20% (w/v) based on the first hydrogel layer, where the first hydrogel layer is a dried hydrogel.

7. The microneedle patch of claim 1, wherein a content of the silk fibroin is in a range of 40 to 70% (w/v) based on the second hydrogel layer, where the first hydrogel layer is a dried hydrogel.

8. The microneedle patch of claim 1, wherein a ratio between a thickness of the first hydrogel layer and a thickness of the second hydrogel layer is in a range of 2:8 to 8:2, wherein the first hydrogel layer and the second hydrogel layer are dried hydrogel layers.

9. A tissue adhesive including the microneedle patch according to claim 1.

10. A method of treating a wound of a patient, the method comprising:
    contacting the microneedle patch of claim 1 with the wound of the patient.

* * * * *

SEQUENCE LISTING

```
<160> NUMBER OF SEQ ID NOS: 16

<210> SEQ ID NO 1
<211> LENGTH: 800
<212> TYPE: PRT
<213> ORGANISM: Artificial Sequence
<220> FEATURE:
<223> OTHER INFORMATION: fp-1

<400> SEQUENCE: 1

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
                20                  25                  30

Pro Ser Tyr Pro Pro Thr Tyr Lys Ala Lys Pro Ser Tyr Pro Pro Thr
            35                  40                  45

Tyr Lys Ala Lys Pro Ser Tyr Pro Pro Thr Tyr Lys Ala Lys Pro Ser
        50                  55                  60

Tyr Pro Pro Thr Tyr Lys Ala Lys Pro Ser Tyr Pro Pro Thr Tyr Lys
65                  70                  75                  80

Ala Lys Pro Ser Tyr Pro Pro Thr Tyr Lys Ala Lys Pro Ser Tyr Pro
                85                  90                  95
```

```
Pro Thr Tyr Lys Ala Lys Pro Ser Tyr Pro Pro Thr Tyr Lys Ala Lys
                100                 105                 110

Pro Ser Tyr Pro Pro Thr Tyr Lys Ala Lys Pro Ser Tyr Pro Pro Thr
            115                 120                 125

Tyr Lys Ala Lys Pro Ser Tyr Pro Pro Thr Tyr Lys Ala Lys Pro Ser
        130                 135                 140

Tyr Pro Pro Thr Tyr Lys Ala Lys Pro Ser Tyr Pro Pro Thr Tyr Lys
145                 150                 155                 160

Ala Lys Pro Ser Tyr Pro Pro Thr Tyr Lys Ala Lys Pro Ser Tyr Pro
                165                 170                 175

Pro Thr Tyr Lys Ala Lys Pro Ser Tyr Pro Pro Thr Tyr Lys Ala Lys
                180                 185                 190

Pro Ser Tyr Pro Pro Thr Tyr Lys Ala Lys Pro Ser Tyr Pro Pro Thr
            195                 200                 205

Tyr Lys Ala Lys Pro Ser Tyr Pro Pro Thr Tyr Lys Ala Lys Pro Ser
        210                 215                 220

Tyr Pro Pro Thr Tyr Lys Ala Lys Pro Ser Tyr Pro Pro Thr Tyr Lys
225                 230                 235                 240

Ala Lys Pro Ser Tyr Pro Pro Thr Tyr Lys Ala Lys Pro Ser Tyr Pro
                245                 250                 255

Pro Thr Tyr Lys Ala Lys Pro Ser Tyr Pro Pro Thr Tyr Lys Ala Lys
                260                 265                 270

Pro Ser Tyr Pro Pro Thr Tyr Lys Ala Lys Pro Ser Tyr Pro Pro Thr
            275                 280                 285

Tyr Lys Ala Lys Pro Ser Tyr Pro Pro Thr Tyr Lys Ala Lys Pro Ser
        290                 295                 300

Tyr Pro Pro Thr Tyr Lys Ala Lys Pro Ser Tyr Pro Pro Thr Tyr Lys
305                 310                 315                 320

Ala Lys Pro Ser Tyr Pro Pro Thr Tyr Lys Ala Lys Pro Ser Tyr Pro
                325                 330                 335

Pro Thr Tyr Lys Ala Lys Pro Ser Tyr Pro Pro Thr Tyr Lys Ala Lys
                340                 345                 350

Pro Ser Tyr Pro Pro Thr Tyr Lys Ala Lys Pro Ser Tyr Pro Pro Thr
            355                 360                 365

Tyr Lys Ala Lys Pro Ser Tyr Pro Pro Thr Tyr Lys Ala Lys Pro Ser
        370                 375                 380

Tyr Pro Pro Thr Tyr Lys Ala Lys Pro Ser Tyr Pro Pro Thr Tyr Lys
385                 390                 395                 400

Ala Lys Pro Ser Tyr Pro Pro Thr Tyr Lys Ala Lys Pro Ser Tyr Pro
                405                 410                 415

Pro Thr Tyr Lys Ala Lys Pro Ser Tyr Pro Pro Thr Tyr Lys Ala Lys
                420                 425                 430

Pro Ser Tyr Pro Pro Thr Tyr Lys Ala Lys Pro Ser Tyr Pro Pro Thr
            435                 440                 445

Tyr Lys Ala Lys Pro Ser Tyr Pro Pro Thr Tyr Lys Ala Lys Pro Ser
        450                 455                 460

Tyr Pro Pro Thr Tyr Lys Ala Lys Pro Ser Tyr Pro Pro Thr Tyr Lys
465                 470                 475                 480

Ala Lys Pro Ser Tyr Pro Pro Thr Tyr Lys Ala Lys Pro Ser Tyr Pro
                485                 490                 495

Pro Thr Tyr Lys Ala Lys Pro Ser Tyr Pro Pro Thr Tyr Lys Ala Lys
                500                 505                 510

Pro Ser Tyr Pro Pro Thr Tyr Lys Ala Lys Pro Ser Tyr Pro Pro Thr
```

```
                515                 520                 525
Tyr Lys Ala Lys Pro Ser Tyr Pro Pro Thr Tyr Lys Ala Lys Pro Ser
            530                 535                 540

Tyr Pro Pro Thr Tyr Lys Ala Lys Pro Ser Tyr Pro Pro Thr Tyr Lys
545                 550                 555                 560

Ala Lys Pro Ser Tyr Pro Pro Thr Tyr Lys Ala Lys Pro Ser Tyr Pro
                565                 570                 575

Pro Thr Tyr Lys Ala Lys Pro Ser Tyr Pro Pro Thr Tyr Lys Ala Lys
            580                 585                 590

Pro Ser Tyr Pro Pro Thr Tyr Lys Ala Lys Pro Ser Tyr Pro Pro Thr
        595                 600                 605

Tyr Lys Ala Lys Pro Ser Tyr Pro Pro Thr Tyr Lys Ala Lys Pro Ser
610                 615                 620

Tyr Pro Pro Thr Tyr Lys Ala Lys Pro Ser Tyr Pro Pro Thr Tyr Lys
625                 630                 635                 640

Ala Lys Pro Ser Tyr Pro Pro Thr Tyr Lys Ala Lys Pro Ser Tyr Pro
                645                 650                 655

Pro Thr Tyr Lys Ala Lys Pro Ser Tyr Pro Pro Thr Tyr Lys Ala Lys
            660                 665                 670

Pro Ser Tyr Pro Pro Thr Tyr Lys Ala Lys Pro Ser Tyr Pro Pro Thr
        675                 680                 685

Tyr Lys Ala Lys Pro Ser Tyr Pro Pro Thr Tyr Lys Ala Lys Pro Ser
690                 695                 700

Tyr Pro Pro Thr Tyr Lys Ala Lys Pro Ser Tyr Pro Pro Thr Tyr Lys
705                 710                 715                 720

Ala Lys Pro Ser Tyr Pro Pro Thr Tyr Lys Ala Lys Pro Ser Tyr Pro
                725                 730                 735

Pro Thr Tyr Lys Ala Lys Pro Ser Tyr Pro Pro Thr Tyr Lys Ala Lys
            740                 745                 750

Pro Ser Tyr Pro Pro Thr Tyr Lys Ala Lys Pro Ser Tyr Pro Pro Thr
        755                 760                 765

Tyr Lys Ala Lys Pro Ser Tyr Pro Pro Thr Tyr Lys Ala Lys Pro Ser
770                 775                 780

Tyr Pro Pro Thr Tyr Lys Ala Lys Pro Ser Tyr Pro Pro Thr Tyr Lys
785                 790                 795                 800

<210> SEQ ID NO 2
<211> LENGTH: 10
<212> TYPE: PRT
<213> ORGANISM: Artificial Sequence
<220> FEATURE:
<223> OTHER INFORMATION: fp-1 variant

<400> SEQUENCE: 2

Ala Lys Pro Ser Tyr Pro Pro Thr Tyr Lys
1               5                   10

<210> SEQ ID NO 3
<211> LENGTH: 120
<212> TYPE: PRT
<213> ORGANISM: Artificial Sequence
<220> FEATURE:
<223> OTHER INFORMATION: fp-1 variant

<400> SEQUENCE: 3

Ala Lys Pro Ser Tyr Pro Pro Thr Tyr Lys Ala Lys Pro Ser Tyr Pro
1               5                   10                  15
```

```
Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
        35                  40                  45

Tyr Lys Ala Lys Pro Ser Tyr Pro Pro Thr Tyr Lys Ala Lys Pro Ser
 50                  55                  60

Tyr Pro Pro Thr Tyr Lys Ala Lys Pro Ser Tyr Pro Pro Thr Tyr Lys
 65                  70                  75                  80

Ala Lys Pro Ser Tyr Pro Pro Thr Tyr Lys Ala Lys Pro Ser Tyr Pro
            85                  90                  95

Pro Thr Tyr Lys Ala Lys Pro Ser Tyr Pro Pro Thr Tyr Lys Ala Lys
            100                 105                 110

Pro Ser Tyr Pro Pro Thr Tyr Lys
            115                 120

<210> SEQ ID NO 4
<211> LENGTH: 472
<212> TYPE: PRT
<213> ORGANISM: Artificial Sequence
<220> FEATURE:
<223> OTHER INFORMATION: fp-2

<400> SEQUENCE: 4

Leu Phe Ser Phe Phe Leu Leu Thr Cys Thr Gln Leu Cys Leu Gly
1               5                   10                  15

Thr Asn Arg Pro Asp Tyr Asn Asp Asp Glu Glu Asp Asp Tyr Lys Pro
            20                  25                  30

Pro Val Tyr Lys Pro Ser Pro Ser Lys Tyr Arg Pro Val Asn Pro Cys
            35                  40                  45

Leu Lys Lys Pro Cys Lys Tyr Asn Gly Val Cys Lys Pro Arg Gly Gly
 50                  55                  60

Ser Tyr Lys Cys Phe Cys Lys Gly Gly Tyr Tyr Gly Tyr Asn Cys Asn
65                  70                  75                  80

Leu Lys Asn Ala Cys Lys Pro Asn Gln Cys Lys Asn Lys Ser Arg Cys
            85                  90                  95

Val Pro Val Gly Lys Thr Phe Lys Cys Val Cys Arg Asn Gly Asn Phe
            100                 105                 110

Gly Arg Leu Cys Glu Lys Asn Val Cys Ser Pro Asn Pro Cys Lys Asn
            115                 120                 125

Asn Gly Lys Cys Ser Pro Leu Gly Lys Thr Gly Tyr Lys Cys Thr Cys
 130                 135                 140

Ser Gly Gly Tyr Thr Gly Pro Arg Cys Glu Val His Ala Cys Lys Pro
145                 150                 155                 160

Asn Pro Cys Lys Asn Lys Gly Arg Cys Phe Pro Asp Gly Lys Thr Gly
            165                 170                 175

Tyr Lys Cys Arg Cys Val Asp Gly Tyr Ser Gly Pro Thr Cys Gln Glu
            180                 185                 190

Asn Ala Cys Lys Pro Asn Pro Cys Ser Asn Gly Gly Thr Cys Ser Ala
            195                 200                 205

Asp Lys Phe Gly Asp Tyr Ser Cys Glu Cys Arg Pro Gly Tyr Phe Gly
 210                 215                 220

Pro Glu Cys Glu Arg Tyr Val Cys Ala Pro Asn Pro Cys Lys Asn Gly
225                 230                 235                 240

Gly Ile Cys Ser Ser Asp Gly Ser Gly Gly Tyr Arg Cys Arg Cys Lys
            245                 250                 255
```

Gly Gly Tyr Ser Gly Pro Thr Cys Lys Val Asn Val Cys Lys Pro Thr
            260                 265                 270

Pro Cys Lys Asn Ser Gly Arg Cys Val Asn Lys Gly Ser Ser Tyr Asn
            275                 280                 285

Cys Ile Cys Lys Gly Gly Tyr Ser Gly Pro Thr Cys Gly Glu Asn Val
            290                 295                 300

Cys Lys Pro Asn Pro Cys Gln Asn Arg Gly Arg Cys Tyr Pro Asp Asn
305                 310                 315                 320

Ser Asp Asp Gly Phe Lys Cys Arg Cys Val Gly Gly Tyr Lys Gly Pro
                    325                 330                 335

Thr Cys Glu Asp Lys Pro Asn Pro Cys Asn Thr Lys Pro Cys Lys Asn
            340                 345                 350

Gly Gly Lys Cys Asn Tyr Asn Gly Lys Ile Tyr Thr Cys Lys Cys Ala
            355                 360                 365

Tyr Gly Trp Arg Gly Arg His Cys Thr Asp Lys Ala Tyr Lys Pro Asn
            370                 375                 380

Pro Cys Val Val Ser Lys Pro Cys Lys Asn Arg Gly Lys Cys Ile Trp
385                 390                 395                 400

Asn Gly Lys Ala Tyr Arg Cys Lys Cys Ala Tyr Gly Tyr Gly Gly Arg
                    405                 410                 415

His Cys Thr Lys Lys Ser Tyr Lys Lys Asn Pro Cys Ala Ser Arg Pro
            420                 425                 430

Cys Lys Asn Arg Gly Lys Cys Thr Asp Lys Gly Asn Gly Tyr Val Cys
            435                 440                 445

Lys Cys Ala Arg Gly Tyr Ser Gly Arg Tyr Cys Ser Leu Lys Ser Pro
            450                 455                 460

Pro Ser Tyr Asp Asp Asp Glu Tyr
465                 470

<210> SEQ ID NO 5
<211> LENGTH: 50
<212> TYPE: PRT
<213> ORGANISM: Artificial Sequence
<220> FEATURE:
<223> OTHER INFORMATION: fp-3

<400> SEQUENCE: 5

Pro Trp Ala Asp Tyr Tyr Gly Pro Lys Tyr Gly Pro Pro Arg Arg Tyr
1               5                   10                  15

Gly Gly Gly Asn Tyr Asn Arg Tyr Gly Arg Arg Tyr Gly Gly Tyr Lys
                20                  25                  30

Gly Trp Asn Asn Gly Trp Lys Arg Gly Arg Trp Gly Arg Lys Tyr Tyr
            35                  40                  45

Gly Ser
    50

<210> SEQ ID NO 6
<211> LENGTH: 750
<212> TYPE: PRT
<213> ORGANISM: Artificial Sequence
<220> FEATURE:
<223> OTHER INFORMATION: fp-4

<400> SEQUENCE: 6

Tyr Gly Arg Arg Tyr Gly Glu Pro Ser Gly Tyr Ala Asn Ile Gly His
1               5                   10                  15

Arg Arg Tyr Tyr Glu Arg Ala Ile Ser Phe His Arg His Ser His Val
                20                  25                  30

```
His Gly His His Leu Leu His Arg His Val His Arg His Ser Val Leu
        35                  40                  45

His Gly His Val His Met His Arg Val Ser His Arg Ile Met His Arg
        50                  55                  60

His Arg Val Leu His Gly His Val His Arg His Arg Val Leu His Asn
65                  70                  75                  80

His Val His Arg His Ser Val Leu His Gly His Val His Arg His Arg
                85                  90                  95

Val Leu His Arg His Val His Arg His Asn Val Leu His Gly His Val
            100                 105                 110

His Arg His Arg Val Leu His Lys His Val His Asn His Arg Val Leu
            115                 120                 125

His Lys His Leu His Lys His Gln Val Leu His Gly His Val His Arg
        130                 135                 140

His Gln Val Leu His Lys His Val His Asn His Arg Val Leu His Lys
145                 150                 155                 160

His Leu His Lys His Gln Val Leu His Gly His Val His Thr His Arg
                165                 170                 175

Val Leu His Lys His Val His Lys His Arg Val Leu His Lys His Leu
            180                 185                 190

His Lys His Gln Val Leu His Gly His Ile His Thr His Arg Val Leu
        195                 200                 205

His Lys His Leu His Lys His Gln Val Leu His Gly His Val His Thr
        210                 215                 220

His Arg Val Leu His Lys His Val His Lys His Arg Val Leu His Lys
225                 230                 235                 240

His Leu His Lys His Gln Val Leu His Gly His Val His Met His Arg
                245                 250                 255

Val Leu His Lys His Val His Lys His Arg Val Leu His Lys His Val
            260                 265                 270

His Lys His His Val His Lys His Val His Ser His Arg Val Leu
        275                 280                 285

His Lys His Val His Lys His Arg Val Glu His Gln His Val His Lys
        290                 295                 300

His His Val Leu His Arg His Val His Ser His His Val Val His Ser
305                 310                 315                 320

His Val His Lys His Arg Val Val His Ser His Val His Lys His Asn
        325                 330                 335

Val Val His Ser His Val His Arg His Gln Ile Leu His Arg His Val
            340                 345                 350

His Arg His Gln Val Val His Arg His Val His Arg His Leu Ile Ala
        355                 360                 365

His Arg His Ile His Ser His Gln Ala Ala Val His Arg His Val His
        370                 375                 380

Thr His Phe Glu Gly Asn Phe Asn Asp Asp Gly Thr Asp Val Asn Leu
385                 390                 395                 400

Arg Ile Arg His Gly Ile Ile Tyr Phe Gly Gly Asn Thr Tyr Arg Leu
                405                 410                 415

Ser Gly Gly Arg Arg Arg Phe Met Thr Leu Trp Gln Glu Cys Leu Glu
            420                 425                 430

Ser Tyr Gly Asp Ser Asp Glu Cys Phe Val Gln Leu Leu Glu Gly Asn
            435                 440                 445
```

```
Gln His Leu Phe Thr Val Val Gln Gly His His Ser Thr Ser Phe Arg
    450                 455                 460

Ser Asp Leu Ser Asn Asp Leu His Pro Asp Asn Asn Ile Glu Gln Ile
465                 470                 475                 480

Ala Asn Asp His Val Asn Asp Ile Ala Gln Ser Thr Asp Gly Asp Ile
                485                 490                 495

Asn Asp Phe Ala Asp Thr His Tyr Asn Asp Val Ala Pro Ile Ala Asp
            500                 505                 510

Val His Val Asp Asn Ile Ala Gln Thr Ala Asp Asn His Val Lys Asn
        515                 520                 525

Ile Ala Gln Thr Ala His His Val Asn Asp Val Ala Gln Ile Ala
    530                 535                 540

Asp Asp His Val Asn Asp Ile Gly Gln Thr Ala Tyr Asp His Val Asn
545                 550                 555                 560

Asn Ile Gly Gln Thr Ala Asp Asp His Val Asn Asp Ile Ala Gln Thr
                565                 570                 575

Ala Asp Asp His Val Asn Ala Ile Ala Gln Thr Ala Asp Asp His Val
            580                 585                 590

Asn Ala Ile Ala Gln Thr Ala Asp Asp His Val Asn Asp Ile Gly Asp
        595                 600                 605

Thr Ala Asn Ser His Ile Val Arg Val Gln Gly Val Ala Lys Asn His
    610                 615                 620

Leu Tyr Gly Ile Asn Lys Ala Ile Gly Lys His Ile Gln His Leu Lys
625                 630                 635                 640

Asp Val Ser Asn Arg His Ile Glu Lys Leu Asn Asn His Ala Thr Lys
                645                 650                 655

Asn Leu Leu Gln Ser Ala Leu Gln His Lys Gln Gln Thr Ile Glu Arg
            660                 665                 670

Glu Ile Gln His Lys Arg His Leu Ser Glu Lys Glu Asp Ile Asn Leu
        675                 680                 685

Gln His Glu Asn Ala Met Lys Ser Lys Val Ser Tyr Asp Gly Pro Val
    690                 695                 700

Phe Asn Glu Lys Val Ser Val Val Ser Asn Gln Gly Ser Tyr Asn Glu
705                 710                 715                 720

Lys Val Pro Val Leu Ser Asn Gly Gly Tyr Asn Gly Lys Val Ser
                725                 730                 735

Ala Leu Ser Asp Gln Gly Ser Tyr Asn Glu Gly Tyr Ala Tyr
            740                 745                 750

<210> SEQ ID NO 7
<211> LENGTH: 82
<212> TYPE: PRT
<213> ORGANISM: Artificial Sequence
<220> FEATURE:
<223> OTHER INFORMATION: fp-5

<400> SEQUENCE: 7

Lys His His His His His Ser Ser Glu Glu Tyr Lys Gly Gly Tyr
1                 5                  10                  15

Tyr Pro Gly Asn Thr Tyr His Tyr His Ser Gly Gly Ser Tyr His Gly
                20                  25                  30

Ser Gly Tyr His Gly Gly Tyr Lys Gly Lys Tyr Tyr Gly Lys Ala Lys
            35                  40                  45

Lys Tyr Tyr Tyr Lys Tyr Lys Asn Ser Gly Lys Tyr Lys Tyr Leu Lys
        50                  55                  60
```

```
Lys Ala Arg Lys Tyr His Arg Lys Gly Tyr Lys Tyr Tyr Gly Gly
 65                  70                  75                  80

Ser Ser

<210> SEQ ID NO 8
<211> LENGTH: 103
<212> TYPE: PRT
<213> ORGANISM: Artificial Sequence
<220> FEATURE:
<223> OTHER INFORMATION: fp-6

<400> SEQUENCE: 8

Ile Ala Ala Leu Cys Gly Ile Val Lys Ser Ile Asp Ser Asp Ser
  1               5                  10                  15

Asp Tyr Asp Tyr Lys Gly Arg Gly Tyr Cys Thr Asn Lys Gly Cys Arg
                 20                  25                  30

Ser Gly Tyr Asn Tyr Phe Gly Asn Lys Gly Tyr Cys Lys Tyr Gly Glu
             35                  40                  45

Lys Ser Tyr Thr Tyr Asn Cys Asn Ser Tyr Ala Gly Cys Cys Leu Pro
 50                  55                  60

Arg Asn Pro Tyr Gly Lys Leu Lys Tyr Cys Thr Asn Lys Tyr Gly
 65                  70                  75                  80

Cys Pro Asn Asn Tyr Tyr Phe Tyr Asn Asn Lys Gly Tyr Tyr Leu
                 85                  90                  95

Glu His His His His His
            100

<210> SEQ ID NO 9
<211> LENGTH: 199
<212> TYPE: PRT
<213> ORGANISM: Artificial Sequence
<220> FEATURE:
<223> OTHER INFORMATION: fp-151

<400> SEQUENCE: 9

Ala Lys Pro Ser Tyr Pro Pro Thr Tyr Lys Ala Lys Pro Ser Tyr Pro
  1               5                  10                  15

Pro Thr Tyr Lys Ala Lys Pro Ser Tyr Pro Pro Thr Tyr Lys Ala Lys
                 20                  25                  30

Pro Ser Tyr Pro Pro Thr Tyr Lys Ala Lys Pro Ser Tyr Pro Pro Thr
             35                  40                  45

Tyr Lys Ala Lys Pro Ser Tyr Pro Pro Thr Tyr Lys Pro Trp Ser Ser
 50                  55                  60

Glu Glu Tyr Lys Gly Gly Tyr Tyr Pro Gly Asn Thr His Tyr His
 65                  70                  75                  80

Ser Gly Gly Ser Tyr His Gly Ser Gly Tyr His Gly Tyr Lys Gly
                 85                  90                  95

Lys Tyr Tyr Gly Lys Ala Lys Lys Tyr Tyr Lys Tyr Lys Asn Ser
            100                 105                 110

Gly Lys Tyr Lys Tyr Leu Lys Lys Ala Arg Lys Tyr His Arg Lys Gly
            115                 120                 125

Tyr Lys Lys Tyr Gly Gly Gly Ser Ser Ala Lys Pro Ser Tyr Pro
        130                 135                 140

Pro Thr Tyr Lys Ala Lys Pro Ser Tyr Pro Pro Thr Tyr Lys Ala Lys
145                 150                 155                 160

Pro Ser Tyr Pro Pro Thr Tyr Lys Ala Lys Pro Ser Tyr Pro Pro Thr
                165                 170                 175
```

Tyr Lys Ala Lys Pro Ser Tyr Pro Pro Thr Tyr Lys Ala Lys Pro Ser
                180                 185                 190

Tyr Pro Pro Thr Tyr Lys Leu
        195

<210> SEQ ID NO 10
<211> LENGTH: 171
<212> TYPE: PRT
<213> ORGANISM: Artificial Sequence
<220> FEATURE:
<223> OTHER INFORMATION: fp-131

<400> SEQUENCE: 10

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
                20                  25                  30

Pro Ser Tyr Pro Pro Thr Tyr Lys Ala Lys Pro Ser Tyr Pro Pro Thr
            35                  40                  45

Tyr Lys Ala Lys Pro Ser Tyr Pro Pro Thr Tyr Lys Pro Trp Ala Asp
        50                  55                  60

Tyr Tyr Gly Pro Lys Tyr Gly Pro Pro Arg Arg Tyr Gly Gly Gly Asn
65                  70                  75                  80

Tyr Asn Arg Tyr Gly Arg Arg Tyr Gly Gly Tyr Lys Gly Trp Asn Asn
                85                  90                  95

Gly Trp Lys Arg Gly Arg Trp Gly Arg Lys Tyr Tyr Gly Ser Ala Lys
                100                 105                 110

Pro Ser Tyr Pro Pro Thr Tyr Lys Ala Lys Pro Ser Tyr Pro Pro Thr
            115                 120                 125

Tyr Lys Ala Lys Pro Ser Tyr Pro Pro Thr Tyr Lys Ala Lys Pro Ser
        130                 135                 140

Tyr Pro Pro Thr Tyr Lys Ala Lys Pro Ser Tyr Pro Pro Thr Tyr Lys
145                 150                 155                 160

Ala Lys Pro Ser Tyr Pro Pro Thr Tyr Lys Leu
                165                 170

<210> SEQ ID NO 11
<211> LENGTH: 175
<212> TYPE: PRT
<213> ORGANISM: Artificial Sequence
<220> FEATURE:
<223> OTHER INFORMATION: fp-353

<400> SEQUENCE: 11

Pro Trp Ala Asp Tyr Tyr Gly Pro Lys Tyr Gly Pro Pro Arg Arg Tyr
1               5                   10                  15

Gly Gly Gly Asn Tyr Asn Arg Tyr Gly Arg Arg Tyr Gly Gly Tyr Lys
                20                  25                  30

Gly Trp Asn Asn Gly Trp Lys Arg Gly Arg Trp Gly Arg Lys Tyr Tyr
            35                  40                  45

Pro Trp Ser Ser Glu Glu Tyr Lys Gly Gly Tyr Tyr Pro Gly Asn Thr
        50                  55                  60

Tyr His Tyr His Ser Gly Gly Ser Tyr His Gly Ser Gly Tyr His Gly
65                  70                  75                  80

Gly Tyr Lys Gly Lys Tyr Tyr Gly Lys Ala Lys Tyr Tyr Lys
                85                  90                  95

Tyr Lys Asn Ser Gly Lys Tyr Lys Tyr Leu Lys Lys Ala Arg Lys Tyr
                100                 105                 110

His Arg Lys Gly Tyr Lys Lys Tyr Gly Gly Ser Ser Gly Ser Ala
            115                 120                 125
Asp Tyr Tyr Gly Pro Lys Tyr Gly Pro Pro Arg Tyr Gly Gly Gly
        130                 135                 140
Asn Tyr Asn Arg Tyr Gly Arg Arg Tyr Gly Gly Tyr Lys Gly Trp Asn
145                 150                 155                 160
Asn Gly Trp Lys Arg Gly Arg Trp Gly Arg Lys Tyr Tyr Gly Ser
            165                 170                 175

<210> SEQ ID NO 12
<211> LENGTH: 187
<212> TYPE: PRT
<213> ORGANISM: Artificial Sequence
<220> FEATURE:
<223> OTHER INFORMATION: fp-153

<400> SEQUENCE: 12

Ala Lys Pro Ser Tyr Pro Pro Thr Tyr Lys Ala Lys Pro Ser Tyr Pro
1               5                   10                  15
Pro Thr Tyr Lys Ala Lys Pro Ser Tyr Pro Pro Thr Tyr Lys Ala Lys
            20                  25                  30
Pro Ser Tyr Pro Pro Thr Tyr Lys Ala Lys Pro Ser Tyr Pro Pro Thr
        35                  40                  45
Tyr Lys Ala Lys Pro Ser Tyr Pro Pro Thr Tyr Lys Pro Trp Ser Ser
    50                  55                  60
Glu Glu Tyr Lys Gly Gly Tyr Tyr Pro Gly Asn Thr Tyr His Tyr His
65                  70                  75                  80
Ser Gly Gly Ser Tyr His Gly Ser Gly Tyr His Gly Tyr Lys Gly
            85                  90                  95
Lys Tyr Tyr Gly Lys Ala Lys Lys Tyr Tyr Lys Tyr Lys Asn Ser
            100                 105                 110
Gly Lys Tyr Lys Tyr Leu Lys Lys Ala Arg Lys Tyr His Arg Lys Gly
            115                 120                 125
Tyr Lys Lys Tyr Tyr Gly Gly Ser Ser Gly Ser Ala Asp Tyr Tyr Gly
        130                 135                 140
Pro Lys Tyr Gly Pro Pro Arg Arg Tyr Gly Gly Gly Asn Tyr Asn Arg
145                 150                 155                 160
Tyr Gly Arg Arg Tyr Gly Gly Tyr Lys Gly Trp Asn Asn Gly Trp Lys
            165                 170                 175
Arg Gly Arg Trp Gly Arg Lys Tyr Tyr Gly Ser
            180                 185

<210> SEQ ID NO 13
<211> LENGTH: 187
<212> TYPE: PRT
<213> ORGANISM: Artificial Sequence
<220> FEATURE:
<223> OTHER INFORMATION: fp-351

<400> SEQUENCE: 13

Pro Trp Ala Asp Tyr Tyr Gly Pro Lys Tyr Gly Pro Pro Arg Arg Tyr
1               5                   10                  15
Gly Gly Gly Asn Tyr Asn Arg Tyr Gly Arg Arg Tyr Gly Gly Tyr Lys
            20                  25                  30
Gly Trp Asn Asn Gly Trp Lys Arg Gly Arg Trp Gly Arg Lys Tyr Tyr
            35                  40                  45
Pro Trp Ser Ser Glu Glu Tyr Lys Gly Gly Tyr Tyr Pro Gly Asn Thr

```
                    50                  55                  60
Tyr His Tyr His Ser Gly Gly Ser Tyr His Gly Ser Gly Tyr His Gly
 65                  70                  75                  80

Gly Tyr Lys Gly Lys Tyr Tyr Gly Lys Ala Lys Lys Tyr Tyr Tyr Lys
                 85                  90                  95

Tyr Lys Asn Ser Gly Lys Tyr Lys Tyr Leu Lys Lys Ala Arg Lys Tyr
                100                 105                 110

His Arg Lys Gly Tyr Lys Lys Tyr Tyr Gly Gly Ser Ser Gly Ser Ala
                    115                 120                 125

Lys Pro Ser Tyr Pro Pro Thr Tyr Ala Lys Pro Ser Tyr Pro Pro
                130                 135                 140

Thr Tyr Lys Ala Lys Pro Ser Tyr Pro Pro Thr Tyr Lys Ala Lys Pro
145                 150                 155                 160

Ser Tyr Pro Pro Thr Tyr Lys Ala Lys Pro Ser Tyr Pro Pro Thr Tyr
                    165                 170                 175

Lys Ala Lys Pro Ser Tyr Pro Pro Thr Tyr Lys
                180                 185
```

<210> SEQ ID NO 14
<211> LENGTH: 60
<212> TYPE: PRT
<213> ORGANISM: Artificial Sequence
<220> FEATURE:
<223> OTHER INFORMATION: fp-1 variant

<400> SEQUENCE: 14

```
Ala Lys Pro Ser Tyr Pro Pro Thr Tyr Lys Ala Lys Pro Ser Tyr Pro
 1               5                  10                  15

Pro Thr Tyr Lys Ala Lys Pro Ser Tyr Pro Pro Thr Tyr Lys Ala Lys
                20                  25                  30

Pro Ser Tyr Pro Pro Thr Tyr Lys Ala Lys Pro Ser Tyr Pro Pro Thr
            35                  40                  45

Tyr Lys Ala Lys Pro Ser Tyr Pro Pro Thr Tyr Lys
         50                  55                  60
```

<210> SEQ ID NO 15
<211> LENGTH: 196
<212> TYPE: PRT
<213> ORGANISM: Artificial Sequence
<220> FEATURE:
<223> OTHER INFORMATION: fp-151 variant

<400> SEQUENCE: 15

```
Ala Lys Pro Ser Tyr Pro Pro Thr Tyr Lys Ala Lys Pro Ser Tyr Pro
 1               5                  10                  15

Pro Thr Tyr Lys Ala Lys Pro Ser Tyr Pro Pro Thr Tyr Lys Ala Lys
                20                  25                  30

Pro Ser Tyr Pro Pro Thr Tyr Lys Ala Lys Pro Ser Tyr Pro Pro Thr
            35                  40                  45

Tyr Lys Ala Lys Pro Ser Tyr Pro Pro Thr Tyr Lys Ser Ser Glu Glu
         50                  55                  60

Tyr Lys Gly Gly Tyr Tyr Pro Gly Asn Thr Tyr His Tyr His Ser Gly
 65                  70                  75                  80

Gly Ser Tyr His Gly Ser Gly Tyr His Gly Tyr Lys Gly Lys Tyr
                 85                  90                  95

Tyr Gly Lys Ala Lys Lys Tyr Tyr Tyr Lys Tyr Lys Asn Ser Gly Lys
                100                 105                 110
```

```
Tyr Lys Tyr Leu Lys Lys Ala Arg Lys Tyr His Arg Lys Gly Tyr Lys
            115                 120                 125
Lys Tyr Tyr Gly Gly Gly Ser Ser Ala Lys Pro Ser Tyr Pro Pro Thr
        130                 135                 140
Tyr Lys Ala Lys Pro Ser Tyr Pro Pro Thr Tyr Lys Ala Lys Pro Ser
145                 150                 155                 160
Tyr Pro Pro Thr Tyr Lys Ala Lys Pro Ser Tyr Pro Pro Thr Tyr Lys
                165                 170                 175
Ala Lys Pro Ser Tyr Pro Pro Thr Tyr Lys Ala Lys Pro Ser Tyr Pro
            180                 185                 190
Pro Thr Tyr Lys
        195

<210> SEQ ID NO 16
<211> LENGTH: 76
<212> TYPE: PRT
<213> ORGANISM: Artificial Sequence
<220> FEATURE:
<223> OTHER INFORMATION: mgfp-5

<400> SEQUENCE: 16

Ser Ser Glu Glu Tyr Lys Gly Gly Tyr Pro Gly Asn Thr Tyr His
1               5                   10                  15
Tyr His Ser Gly Gly Ser Tyr His Gly Ser Gly Tyr His Gly Gly Tyr
            20                  25                  30
Lys Gly Lys Tyr Tyr Gly Lys Ala Lys Lys Tyr Tyr Tyr Lys Tyr Lys
        35                  40                  45
Asn Ser Gly Lys Tyr Lys Tyr Leu Lys Lys Ala Arg Lys Tyr His Arg
    50                  55                  60
Lys Gly Tyr Lys Lys Tyr Tyr Gly Gly Gly Ser Ser
65                  70                  75
```